US011421266B2

(12) United States Patent
Bergmann et al.

(10) Patent No.: US 11,421,266 B2
(45) Date of Patent: Aug. 23, 2022

(54) SET OF OLIGONUCLEOTIDE PROBES AS WELL AS METHODS AND USES THERETO

(71) Applicant: Roche Molecular Systems, Inc., Pleasanton, CA (US)

(72) Inventors: Frank Bergmann, Iffeldorf (DE); Walter Eberle, Bernried (DE); Thomas Fischer, Munich (DE); Herbert von der Eltz, Weilheim (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 87 days.

(21) Appl. No.: 16/830,050

(22) Filed: Mar. 25, 2020

(65) Prior Publication Data

US 2020/0277662 A1 Sep. 3, 2020

Related U.S. Application Data

(60) Continuation of application No. 15/136,532, filed on Apr. 22, 2016, now Pat. No. 10,640,815, which is a continuation of application No. 13/862,530, filed on Apr. 15, 2013, now Pat. No. 9,347,091, which is a division of application No. 13/361,549, filed on Jan. 30, 2012, now Pat. No. 8,445,206, which is a continuation of application No. PCT/EP2010/004570, filed on Jul. 26, 2010.

(30) Foreign Application Priority Data

Jul. 30, 2009 (EP) .................................... 09009970

(51) Int. Cl.
*C07H 21/02* (2006.01)
*C12Q 1/6841* (2018.01)
*C12Q 1/6876* (2018.01)
*C12Q 1/6886* (2018.01)

(52) U.S. Cl.
CPC ......... *C12Q 1/6841* (2013.01); *C12Q 1/6876* (2013.01); *C12Q 1/6886* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS

| 5,525,465 | A | * | 6/1996 | Haralambidis | ...... | C12Q 1/6813 |
| | | | | | | 435/6.12 |
| 5,532,129 | A | | 7/1996 | Heller | | |
| 5,552,540 | A | * | 9/1996 | Haralambidis | ........ | C07H 21/00 |
| | | | | | | 536/25.32 |
| 8,445,206 | B2 | | 5/2013 | Bergmann et al. | | |
| 2002/0177127 | A1 | | 11/2002 | Yang et al. | | |
| 2005/0266407 | A1 | | 12/2005 | Chee et al. | | |
| 2007/0037152 | A1 | | 2/2007 | Drmanac | | |

| 2007/0111960 | A1 | * | 5/2007 | Stender | .................. | C12Q 1/708 |
| | | | | | | 514/44 R |
| 2007/0161015 | A1 | | 7/2007 | Zheng et al. | | |
| 2007/0238125 | A1 | | 10/2007 | Uematsu et al. | | |

FOREIGN PATENT DOCUMENTS

| EP | 03132199 | 4/1989 |
| WO | 1993006245 | 4/1993 |
| WO | 1996000234 | 1/1996 |
| WO | 2007059816 A1 | 5/2007 |
| WO | 2008119084 A1 | 10/2008 |

OTHER PUBLICATIONS

Behrens, Sebastian et al., "The Effect of Nucleobase-Specific Fluorescence Quenching on In Situ Hybridization with rRNA-Targeted Oligonucleotide Probes," Systematic & Applied Microbiology, 2004, pp. 565-572, vol. 27.
Best, Michael D., "Click Chemistry and Bioorthogonal Reactions: Unprecedented Selectivity in the Labeling of Biological Molecules," Biochemistry, 2009, pp. 6571-6584, vol. 48.
Grzybowski, J., et al., Synthesis and antibody-mediated detection of oligonucleotides containing multiple 2,4-dinitrophenyl reporter groups, Nucl Acids Res, (1993), 1705-1712, vol. 21 Issue 8.
Gupta, Deepali et al., "Comparison of Fluorescence and Chromogenic In Situ Hybridization for Detection of HER-2/neu Oncogene in Breast Cancer," American Journal of Clinical Pathology, 2003, pp. 381-387, vol. 119.
Ji, Hanlee et al., "Molecular Inversion Probe Analysis of Gene Copy Alterations Reveals Distinct Categories of Colorectal Carcinoma," Cancer Research, Aug. 15, 2006, pp. 7910-7919, vol. 66, No. 16.
Jin, Long et al., "In Situ Hybridization: Detection of DNA and RNA," Morphology Methods: Cell and Molecular Biology Techniques, 2001, pp. 27-46, Humana Press, Totowa, NJ.
Kricka, Larry J., "Stains, labels and detection strategies for nucleic acids assays," Annual Review of Clinical Biochemistry, 2002, pp. 114-129, vol. 39.
Lee, SangHoon et al., "Use of multiple 16S rRNA-targeted fluorescent probes to increase signal strength and measure cellular RNA from natural planktonic bacteria," Marine Ecology Progress Series, Nov. 4, 1993, pp. 193-201, vol. 101.
Liehr et al, "Multicolor chromosome banding (MCB) with YAC/BAC-based probes and region-specific microdissection DNA libraries", Cytogenet Genome Res, 2002, pp. 43-50, v. 97.
Lloyd. Ricardo and Jin. Long. "In Situ Hybridization Analysis of Chromogranin A and B mRNAs in Neuroendocrine Tumors with Digoxigenin-Labeled Oligonucleotide Probe Coctails." Diagnostic Molecular Pathology. 1995. vol. 4. No. 02, pp. 143-151.

(Continued)

*Primary Examiner* — Frank W Lu
(74) *Attorney, Agent, or Firm* — Charney IP Law LLC; Thomas M. Finetti

(57) ABSTRACT

The present disclosure relates to a set of at least 100 single-stranded oligonucleotide probes directed against (or complementary to) portions of a genomic target sequence of interest. The present disclosure also relates to a method of detecting a genomic target sequence of interest using the set of oligonucleotide probes and a method of generating the set of oligonucleotide probes. Further, the present disclosure relates to a kit comprising the set of oligonucleotide probes and at least one further component.

19 Claims, 11 Drawing Sheets

Specification includes a Sequence Listing.

(56) References Cited

OTHER PUBLICATIONS

Mabruk et al., "A rapid microwave-in situ hybridization method for the definitive diagnosis of oral hairy leukoplakia: comparison with immunohistochemistry", Journal of Oral Pathology & Medicine, ; 25(4):170-6, Apr. 1996.

Perletie, John and Tan, Weihong, "Real-Time Monitoring of Intracellular mRNA Hybridization Inside Single Living Cells," Analytical Chemistry, Nov. 15, 2001, pp. 5544-5550, vol. 73, No. 22.

Ross, Jeffrey S. et al., "Targeted Therapy in Breast Cancer The HER-2/neu Gene and Protein," Molecular & Cellular Proteomics, 2004, pp. 379-398, vol. 3, No. 4.

Silverman, Adam P. and Kool, Eric T., "Oligonucleotide Probes for RNA-Targeted Fluorescence in Situ Hybridization," Advances in Clinical Chemistry, 2007, pp. 79-115, vol. 43.

Stratagene Catalog 1988, p. 39.

Ventana Medical Systems, Inc., 2007, Brochure "In situ Hybridization Reagents: Inform (TM) HER2 SISH".

Vizi, Sandor et al., "Methods for quantification of in situ hybridization signals obtained by film autoradiography andphosphorimaging applied for estimation of regional levels of calmodulin mRNA classes in the rat brain," Brain Research Protocols, 2001, pp. 32-44, vol. 8, No. 1.

Weise, A. et al., "Multitude multicolor chromosome banding (mMCB)—a comprehensive one-step multicolor FISH banding method," Cytogenetic and Genome Research, 2003, pp. 34-39, vol. 103.

Weiss, Lawrence M. et al., "Detection of Immunoglobulin Light-chain mRNA in Lymphoid Tissues Using a Practical In Situ Hybridization Method," American Journal of Pathology, Oct. 1990, pp. 979-988, vol. 137, No. 4.

Wiegant, J. et al., "Multiple and sensitive fluorescence in situ hybridization with rhodamine-, fluorescein-, and coumarin-labeled DNAs," Cytogenetic and Cell Genetics, 1993, pp. 73-76, vol. 63.

Wisden, W. and Morris, B. J., "In Situ Hybridization with Oligonucleotide Probes," International Review of Neurobiology, 2002, pp. 3-57, vol. 47, Chapter 1.

Zwirglmaier, Katrin, "Fluorescence in situ hybridisation (FISH)—the next generation," FEMS Microbiology Letters, 2005, pp. 151-158, vol. 246.

\* cited by examiner

Pool 1  15 plates

Pool 2  plates 1-4 + 12-15

Pool 3  plates 5-12

Pool 4  plates 1, 3, 5, 7, 9, 11, 13, 15

Pool 5  plates 1, 6, 11, 15

1 plate = 96 oligos in 8 pools of 12

Pool 6  15 plates, every 2nd pool of 12

→ 4 pools/plate

Pool 7  15 plates, every 4th pool of 12

→ 2 pools/plate

Pool 8  15 plates, every 8th pool of 12

→ 1 pool/plate

Ventana ca. ~15000 labels

Pool 1: 15 plates    8640 labels

Pool 2: plates 1-4 + 12-15

4608 labels

Pool 4: plates 1, 3, 5, 7, 9, 11, 13, 15

4608 labels

Fig. 5A

| Her2 0001 | XTCACCTTTCGACCTCTXGCTCCAAAACACACTCXTTTGTTTTTCTTGAGAXAACCTGCTGATAAATAXTCTGTACTTCGATGCTXT | (SEQ ID No.: 1) |
|---|---|---|
| Her2 0002 | XTACGTTTACACACAGCXCCTAAATTTATTCAGGXCGTCTCTTCTGGAACGXAGATGTAAGCTGATTTXTGTATTCATTTGCCCCXT | (SEQ ID No.: 2) |
| Her2 0003 | XCCTGAGCTTTCATCCTXGAAGGCGAGGAGAAGCXTAGATCCGCCACAAAAXGGATAAGCCCTTCCCCXACCACTAACGGAGGAAXT | (SEQ ID No.: 3) |
| Her2 0004 | XCAGGCCTCGCGCCGCTXGGATATTAAACCTGCCXGGCCGGTAGCTTTCGGXCTCCCCTGCGGAAACCXGCCATTTTTTTTTATXT | (SEQ ID No.: 4) |
| Her2 0005 | XATGACTAGATTTTCAAXAGGCTATTGGTATCAGXGAGTGTCTTATGAAAGXATAAGTTTAACCTGAGXATACTAGATGCAATAAXT | (SEQ ID No.: 5) |

SET OF OLIGONUCLEOTIDE PROBES AS WELL AS METHODS AND USES THERETO

CROSS-REFERENCE TO RELATED APPLICATIONS

This application is a continuation of U.S. application Ser. No. 15/136,532, now U.S. Pat. No. 10,640,815, filed on Apr. 22, 2016 which disclosure is a continuation of U.S. application Ser. No. 13/862,530, now U.S. Patent No. 9,347,091, filed Apr. 15, 2013, which is a divisional of U.S. application Ser. No. 13/361,549, now U.S. Pat. No. 8,445,206, which is a continuation of International Application No. PCT/EP2010/004570, filed Jul. 26, 2010, which claims the benefit of European Patent Application No. 09009970.6, filed Jul. 30, 2009, the disclosures of which are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jan. 30, 2012, is named SEQUENCE_LISTING_26169US.txt, and is 1573 bytes in size.

FIELD OF THE DISCLOSURE

The present disclosure relates to oligonucleotide probes. More specifically, the present disclosure relates to a set of oligonucleotides directed to a genomic target of interest. The present disclosure also relates to methods and kits, comprising a set of oligonucleotides, for detecting a genomic target of interest.

BACKGROUND

The embodiments disclosed herein are not intended to be exhaustive or limit the disclosure to the precise form disclosed in the following detailed description. Rather, the embodiments are chosen and described so that others skilled in the art may utilize their teachings.

In situ hybridization (ISH) is a useful tool in a variety of areas of research and clinical diagnostics. ISH is a technique which combines molecular biological and histochemical techniques aiding in the study of gene expression in tissue sections or cytologic preparations by allowing for the detection and localisation of both DNA and RNA in specific cells. ISH analysis was first described in 1969 and involves a hybridization reaction between a labelled nucleotide probe and a complementary nucleic acid (DNA or RNA within a sample), the hybrids of which can be detected by diverse procedures depending on the nature of the incorporated label. The introduction of nonradioactive probe labelling and detection systems, in the late 1970s, helped in enabling ISH analysis to become feasible in diagnostic pathology laboratories as a molecular diagnostic tool. ISH localizes gene sequences in situ and visualizes the product of gene expression while preserving cell integrity within heterogeneous tissue. An advantage of ISH is its specificity for individual targets in heterogeneous tissue (or cell populations). ISH consists of multiple steps including probe preparation and labelling, tissue preparation, hybridisation, and signal detection.

Southern and slot blotting were the first gene-based HER-2 detection methods used in breast cancer specimens. Fluorescence in situ hybridisation (FISH), which is morphology-driven and can be automated like immunohistochemistry (IHC), has the advantages of a more objective scoring system and the presence of a built-in internal control consisting of the two HER-2 gene signals present in all non-neoplastic cells in the specimen. Disadvantages of FISH include the high costs of each test, longer time required for slide scoring, requirement of a fluorescent microscope, the inability to preserve the slides for storage and review, and occasionally in identifying the invasive tumour cells. So far, two versions of an ISH assay are FDA-approved: the Ventana Inform™ test which measures HER-2 gene copies, and the Abbott-Vysis Pathvysion™ test that includes a chromosome 17 probe in a dual color format.

Chromogenic in situ hybridisation (CISH) may be used with a routine microscope and is relatively low cost and includes a built-in internal control, has objective scoring, and a more robust DNA target. Both FISH and CISH were used to compare 31 cases of infiltrating breast carcinoma with testing performed in laboratories at two institutions and identical results for both methods were found in 26 (84%) of the cases (Gupta et al., 2003, Am. J. Clin. Pathol., 119: 381-387).

Oligonucleotide probes are one form of oligonucleotide probe which these various hybridization techniques may utilize. In general, oligonucleotide probes are usually labelled by 5' or 3' end labelling methods such as the "tailing" of the probe by incorporating a labelled nucleotide. These probes are also generally short in length. The limited amount of label per probe and short length of these probes contributes to these probes often being less sensitive than longer cDNA or antisense RNA probes. Therefore, so far oligonucleotide probes have mostly been used for the detection of highly abundant and/or repetitive gene targets.

SUMMARY OF THE DISCLOSURE

In a first aspect, the present disclosure pertains to a set of oligonucleotide probes comprising at least 100 different single-stranded oligonucleotide probes directed against a genomic target sequence of interest, wherein each of the individual oligonucleotides comprises at least one label. In a further aspect, the disclosure pertains to the use of said set of oligonucleotide probes for detection of a genomic target sequence. In another aspect, the disclosure relates to a method of detecting a genomic target sequence of interest, said method comprising the steps of incubating a set of oligonucleotide probes according to the disclosure with a sample under conditions conducive to the binding of the set of oligonucleotide probes to the genomic target sequence of interest, and detecting the binding of the oligonucleotide probes to the genomic target sequence.

In some embodiments, the set of single stranded oligonucleotide probes may each be complementary to a different subsequence of a genomic target sequence, which may comprise a gene sequence for example. According to some embodiments, each of the single-stranded oligonucleotide probes may be labelled with at least one label. Furthermore, according to some other embodiments of the instant disclosure, the set of oligonucleotide probes may include a subset of probes, each having identical nucleotide sequences. In some embodiments, each probe within a subset may be labelled with the same label at the same location within the probe.

In a further aspect, the disclosure provides a method of generating a set of oligonucleotide probes directed against a genomic target sequence of interest, said method comprising the steps of designing a set of oligonucleotide probes complementary to a plurality of different regions (or subsequences) of the genomic target sequence of interest, and synthesizing the set of oligonucleotide probes.

According to some embodiments, the set of oligonucleotide probes includes 100 or more different probes. In some embodiments, each of the probes is complementary to a different subsequence of the genomic target sequence. Also, in some embodiments, each of the probes includes at least one label.

In yet a further aspect, the disclosure pertains to a kit comprising a set of oligonucleotide probes for detecting a genomic target sequence of interest and, in addition, at least one further component selected from the group consisting of a deparaffinization agent, a pretreatment agent, a washing agent, a detection agent and a product sheet.

According to other embodiments of the present disclosure, a method for detecting a genomic target sequence of interest is provided. The method includes the steps of incubating a set of oligonucleotide probes with a sample under conditions conductive for binding the set of probes to a subsequence of the genomic target sequence, and detecting the bound oligonucleotide probes. According to some embodiments of the instant disclosure, the method is carried out by means of in situ hybridization. In some embodiments the set of oligonucleotide probes consists of 100 or more single stranded oligonucleotide probes having different nucleotide sequences. In some embodiments of the instant disclosure, the genomic target sequence of interest comprises a nucleotide sequence of a particular gene and each of the 100 or more oligonucleotide probes targets a different subsequence of the gene sequence. Furthermore, according to some embodiments of the instant disclosure, each of the 100 or more probes may be labelled with at least one label.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

FIG. 5A presents five different 87mer DNA oligonucleotide probes directed against the human HER-2 gene locus, each comprising 81 nucleotides and 6 DNP phosphoramidite labels (1 at 5'-end and 5 internally incorporated). The position of each label is indicated by "X", wherein X indicates 2,4-dinitrophenyl (DNP). DNP is placed in a 16 nt spacing at positions 2, 19, 36, 53, 70 and 87, as counted from the 3'-terminal end.

Figure 1A:
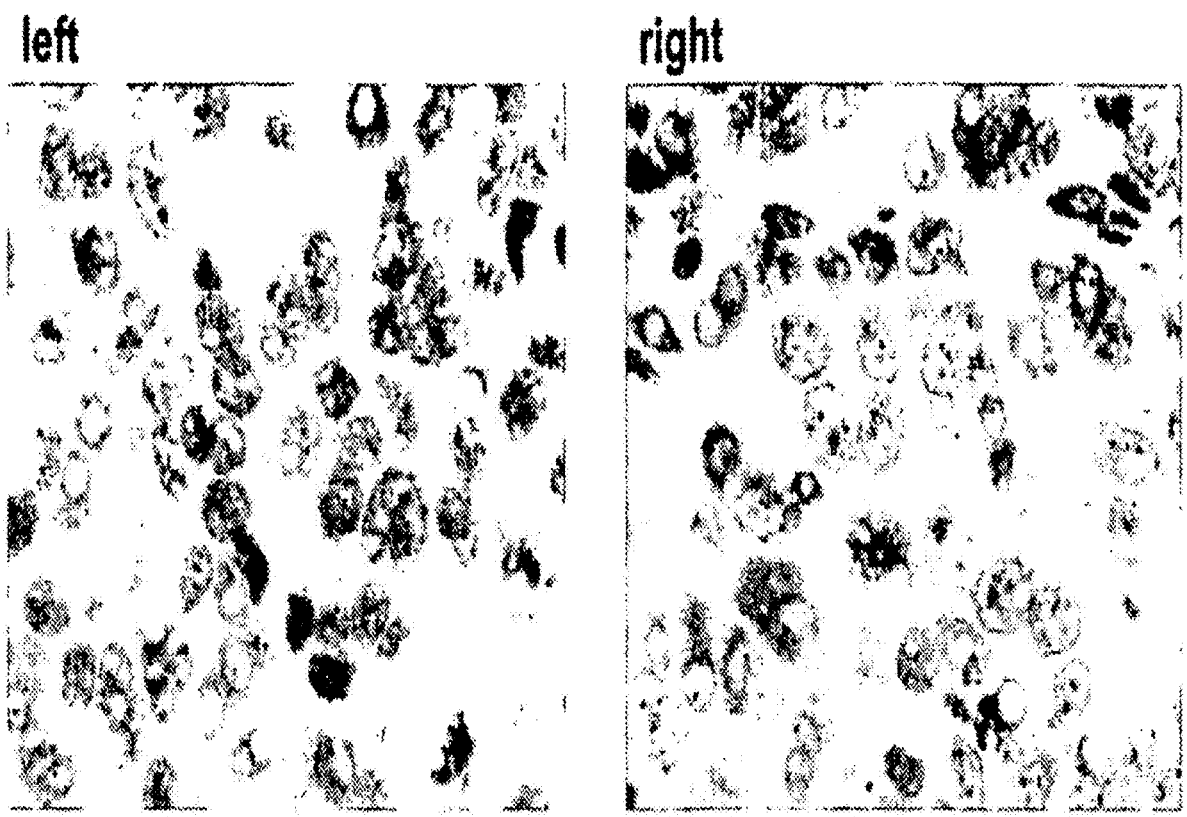
FIG. 1A presents in situ hybridization results, using DNP-labeled oligonucleotide probes at various concentrations, for HER-2 genomic gene sequences in Xenografts derived from Calu3 cells. The left panel presents results obtained utilizing the HER-2/neu probe at a concentration of 10 µg/ml from the Ventana Inform™ detection system (from Ventana Medical Systems, Inc., U.S.A., Cat. No. 780-001). The right panel presents results obtained utilizing a set of 1440 different DNP-labeled oligonucleotide probes at a concentration of 4 µg/ml (each oligonucleotide probe comprised 81 nucleotides and 6 labels).

Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

SEQ ID NO: 1 is the nucleotide sequence for the oligonucleotide probe Her2 Probe 0001.

SEQ ID NO:2 is the nucleotide sequence for the oligonucleotide probe Her2 Probe 0002.

SEQ ID NO:3 is the nucleotide sequence for the oligonucleotide probe Her2 Probe 0003.

SEQ ID NO:4 is the nucleotide sequence for the oligonucleotide probe Her2 Probe 0004.

SEQ ID NO:5 is the nucleotide sequence for the oligonucleotide probe Her2 Probe 0005.

Although the sequence listing represents an embodiment of the present disclosure, the sequence listing is not to be construed as limiting the scope of the disclosure in any manner and may be modified in any manner as consistent with the instant disclosure and as set forth herein.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

In the context of the present disclosure, it has been found that a method using a "cocktail" or "set" of at least 100 different single-stranded oligonucleotide probes that are complementary to different regions of a target molecule is particularly suitable for detecting low abundant genes. In particular, as disclosed herein, the present disclosure provides the surprising discovery that a cocktail according to the instant disclosure is particularly suitable to detect a genomic target sequence of interest in a reduced period of time (see FIGS. 1A, 1B, and 1C) with the need of a reduced amount (e.g., concentration) of probes (see FIGS. 2A, 2B, and 2C) and with higher specificity (see FIGS. 1A, 1B, 1C, 2A, 2B, 2C, 3A, and 3B) as compared to the detection methods currently known in the art. Accordingly, the present disclosure presents a method that is superior to those known and described in the art and that is surprisingly and unexpectedly faster, cheaper, more sensitive, and/or more predictable.

In one aspect, the present disclosure provides a set of oligonucleotide probes comprising at least 100 different single-stranded oligonucleotide probes directed against a genomic target sequence of interest, wherein each of the individual oligonucleotide probes comprises at least one label.

Single-stranded oligonucleotide probes allow for detecting a genomic sequence of interest without requiring a heating step in order to ensure the dissolution of secondary structures, and without concern of re-annealing of the complementary strands of the probe.

The term "oligonucleotide probe" as used herein generally refers to any kind of nucleotide molecule synthesized to match (i.e., be complementary to) a nucleotide sequence of interest which can be used to detect, analyse, and/or visualize said nucleotide sequence on a molecular level. An oligonucleotide probe according to the present disclosure generally refers to a molecule comprising several nucleotides, in general at least 10, 15, and even at least 20 nucleotides, for example, and having at least one label. Optionally, the oligonucleotide probe may also comprise any suitable non-nucleotide units and/or linking reagent which may be suitable to incorporate the label. It should be understood that the oligonucleotide probe has a length suitable to provide the required specificity. In general, the probe may be a DNA oligonucleotide probe or a RNA oligonucleotide probe. Further, it should also be understood that a nucleotide includes all kind of structures composed of a nucleobase (i.e. a nitrogenous base), a five carbon sugar which may be either a ribose, a 2'-deoxyribose, or any derivative thereof, and a phosphate group. The nucleobase and the sugar constitute a unit referred to as a nucleoside.

The phosphate groups may form bonds with the 2, 3, or the 5-carbon, in particular with the 3 and 5 carbon of the sugar. In the context of the present disclosure, the term "nucleotide" may equally refer to a ribonucleotide or to a deoxyribonucleotide. A ribonucleotide contains a ribose as a sugar moiety, while a deoxyribonucleotide contains a deoxyribose as a sugar moiety. Nucleotides can contain either a purine or a pyrimidine base. Accordingly, the oligonucleotide probes of the present disclosure may be constituted by ribonucleotides or deoxyribonucleotides, or by any combination thereof, and may further include one or more modified nucleotide(s).

Optionally, the oligonucleotide probes may further comprise only modified nucleotides. Ribo- and deoxyforms of modified nucleotides may include, but are not limited to, 5-propynyl-uridine, 5-propynyl cytidine, 5-methyl-cytidine, 2-amino-adenosine, 4-thiouridine, 5-iodouridine, N6-methyladenosine, 5-fluorouridine, inosine, 7-propynyl-8-aza-7-deazapurine and 7-halo-8-aza-7-deazapurine nucleosides, for example. The oligonucleotide probes of the disclosure may further comprise backbone modifications such as, e.g., 2'-O-methyl (2'-OMe) RNA, 2'-fluoro (2'-F) DNA, peptide nucleic acids (PNA), or locked nucleic acids (LNA). 2'-OMe RNA is a suitable backbone modification because it hybridizes strongly (in some cases more strongly than DNA) and is extremely stable to RNases and DNases.

LNA is a class of conformationally restricted oligonucleotide analogs in which a ribonucleoside is linked with a methylene group between the 2'-0 and the 4'-C. It resembles natural nucleic acids with respect to base-pairing and duplex formation, but in general LNA duplexes are thermally more stable as compared to the respective DNA or RNA duplex.

Optionally, the oligonucleotide probes of the disclosure may further comprise one or more modification(s) on the phosphate backbone such as phosphothioates or methyl phosphonates, for example, which increase the stability against nucleases.

A set of oligonucleotide probes according to the present disclosure means a pool of oligonucleotides. In general, as used herein, a "set" of oligonucleotides, as referred to herein, means at least 100 different oligonucleotides. In some cases a "set" of oligonucleotides may refer to only approximately 100 different oligonucleotides (such as 96 different oligonucleotides, for example). These oligonucleotides may either differ in one or more nucleotide position(s), or may differ from each other in their complete sequence. Further, these oligonucleotides may comprise the same, or different lengths.

According to some embodiments of the instant disclosure, the set of oligonucleotide probes may comprises more than 100 different oligonucleotides, for example at least 150, 200, 250, 300, 350, 400, 500, 550, 600, 650, 700, 750, 800, 850, 900, 950, or 1000 different oligonucleotides.

According to some embodiments, the set of oligonucleotide probes may comprise at least 1000 different oligonucleotide probes, for example at least 1500, 2000, 2500, 3000, 3500, 4000, 4500, or 5000 different oligonucleotide probes.

Accordingly, in an exemplary embodiment, the set of oligonucleotide probes of the present disclosure may comprise at least 200, 300 or 400 different oligonucleotide probes. In some embodiments, the set of oligonucleotide probes comprises at least 500 different oligonucleotide probes, and in some embodiments the set includes at least 1000 different oligonucleotide probes. As demonstrated and disclosed herein, the sensitivity and specificity (of the detection methods according to the present disclosure) surprisingly and unexpectedly increases with the increasing number of different oligonucleotide probes (even at reduced concentrations and hybridization time periods, see FIGS. 1A, 1B, 1C, 2A, 2B, 2C, 3A, and 3B, for example).

Moreover, the set of oligonucleotide probes according to the present disclosure is further characterized in that each of the oligonucleotide probes has a defined length. This length is constituted by a defined number of nucleotides, optionally further including a defined number of non-nucleotide linking reagents. The generation of oligonucleotide probes with a defined length provide an advantage over the methods known in the art which employ fragmentation steps and thus result in the generation of oligonucleotide probes with a random length distribution. The set of oligonucleotide probes of the present disclosure may be characterized in that each of the oligonucleotide probes has a defined length of from approximately 20 to approximately 200 nucleotides. According to some embodiments, each of the oligonucleotide probes has a defined length of from approximately 40 to approximately 175 nucleotides, or from approximately 60 to approximately 150 nucleotides, or from approximately 80 to approximately 120 nucleotides.

Further, according to some embodiments, the upper and lower nucleotide approximations may be combined in order to arrive at different ranges. For example, oligonucleotide probes comprising a set, as described herein, may have lengths from approximately 20 to approximately 150, or from approximately 60 to approximately 120, or from approximately 80 to approximately 150, or from approximately 30 to approximately 180, for example. In some embodiments of the present disclosure, a set of oligonucleotide probes may comprise oligonucleotide probes having all the same length, or may comprise oligonucleotide probes with different lengths. A set may also comprise some oligonucleotides of the same length and some oligonucleotides or different lengths.

In some embodiments, the set of oligonucleotide probes of the present disclosure may be characterized in that each of the oligonucleotide probes has a length of from approximately 20 to approximately 200 nucleotides or from approximately 40 to approximately 175 nucleotides or from approximately 60 to approximately 150 nucleotides or from approximately 80 to approximately 120 nucleotides.

Oligonucleotide probes with a length of about 80 to about 120 nucleotides, for example, have been found to be well suitable for detecting a genomic target sequence according to the present disclosure. As such, according to some embodiments of the present disclosure, each of the oligonucleotide probes of the set of oligonucleotide probes has a length of approximately 80 to approximately 120 nucleotides.

Further, according to the instant disclosure, the set of oligonucleotide probes may comprise a minimal total number of incorporated labels. For example, the shorter the length of some (or all of) the oligonucleotide probes within the set, the more labels per oligonucleotide those shorter probes may have incorporated, attached, conjugated and/or linked to the individual molecules. Additionally, in some embodiments having shorter probes, more oligonucleotide probes may be used in order to provide a set of oligonucleotides for detection of the genomic target sequence of interest under the conditions described herein without increasing the number of labels per oligonucleotide for the shorter probes.

In order to control the incorporation of labels, the oligonucleotide probes of the present disclosure may be generated by chemical synthesis. Chemical synthesis (versus an enzymatic approach) allows for faster and cost-efficient probe generation and provides more control over the exact fragment length, sequence number and positions of labels. For example, in the context of the present disclosure, it has been found that oligonucleotide probes comprising at least five labels (in presence of about 80 to 90 nucleotides) may be used. Further, the oligonucleotide probes may comprise eight or more labels, in the presence of about 80 to 90 nucleotides, may also be utilized according to the instant disclosure.

Figure 5B:
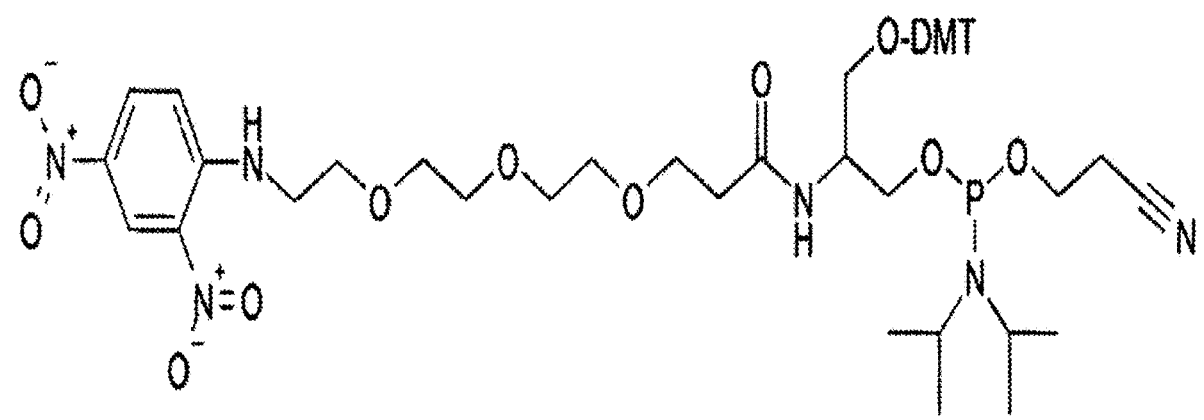
FIG. 5B is a schematic depicting the chemical structure of a phosphoramidite modified building block linked to 2,4-dinitrophenyl (X). DMP indicates dimethoxytrityl.

Referring to FIG. 5A, exemplary oligonucleotide probe sequences according to the instant disclosure are shown. The exemplary probes presented in FIG. 5 include "X"s to represent the incorporation of a defined number of labels along the nucleotide sequence. As illustrated in FIG. 5A, six labels are incorporated in each of the oligonucleotide probe sequences (SED ID Nos.: 1, 2, 3, 4, and 5) at the following positions: prior to nucleotide 1; between nucleotides 16 and 17; between nucleotides 32 and 33; between nucleotides 48 and 49; between nucleotides 64 and 65; and between nucleotides 80 and 81.

Accordingly, in another embodiment, the set of oligonucleotide probes may be characterized in that each of the oligonucleotide probes comprises at least two or three labels, or at least five labels, or at least 10 labels, or even at least 15 labels.

As disclosed herein, the methods and systems disclosed herein demonstrate an increasing sensitivity with the increasing incorporation of labels. However, the incorporation of too many labels may result in interference with successful hybridisation of the probes, and thus with functionality. The present disclosure demonstrates that the presence of approximately 5 to approximately 15 labels per oligonucleotide (dependent on the length of the individual molecule) may establish optimal results.

For example, according to some embodiments, the set of oligonucleotide probes of the present disclosure may be characterized in that (i) each of the oligonucleotide probes has a length of from approximately 20 to approximately 200 nucleotides, or from approximately 40 to approximately 175 nucleotides, or from approximately 60 to approximately 150 nucleotides, or even from approximately 80 to approximately 150 nucleotides, and (ii) each of the oligonucleotide probes comprises at least two or three labels, at least five labels, at least 10 labels, or at least 15 labels.

According to some embodiments each of the oligonucleotide probes comprises at least five labels and has a length of from approximately 20 to approximately 200 nucleotides, for example from 40 to 175 nucleotides or from 60 to 150 nucleotides or even from 80 to 150 nucleotides.

According to some embodiments of the present disclosure, each of the oligonucleotide probes comprises at least 10 labels and has a length of from approximately 20 to approximately 200 nucleotides, for example, from approximately 40 to approximately 175 nucleotides or from approximately 60 to approximately 150 nucleotides or from 80 to 150 nucleotides.

Still in other embodiments of the present disclosure, each of the oligonucleotide probes comprise at least 15 labels and have a length of from approximately 20 to approximately 200 nucleotides, for example, from 40 to 175 nucleotides, or from 60 to 150 nucleotides, or from 80 to 150 nucleotides.

In yet other embodiments of the instant disclosure, each of the oligonucleotide probes may have a length of from approximately 60 to approximately 150 nucleotides and comprises at least two or three labels. In some such embodiments, the probes may include at least five labels or at least 10 labels. In some particular embodiments the probes may include at least 15 labels.

In yet other embodiments of the instant disclosure, the oligonucleotide probes have a length of approximately 80 to approximately 150 nucleotides, and comprise at least two or three labels. In some particular embodiments, the probes comprise at least five labels or even at least 10 or 15 labels.

The term "directed against" as referred to in the context of the present disclosure generally means that the oligonucleotide probe of the present disclosure can bind to a target sequence of interest by means of complementary base pairs. Complementary base pairs are formed between two nucleotide molecules (optionally including modifications) which are complementary to each other. In the context of the present disclosure, the complementary base pairs formed between the oligonucleotide probe and the target sequence may include all kind of canonical or non-canonical base pairs, including, but not limited to, WatsonCrick A-V, Watson-Crick A-T, Watson-Crick G-C, G-V Wobble base pairs, A-V and A-C reverse Hoogsteen base pairs, or purine-purine and pyrimidine-pyrimidine base pairs such as sheared G-A base pairs or G-A imino base pairs.

The phrase "genomic target sequence" as used herein generally refers to a particular region of a genome. Although the instant disclosure may be utilized with prokaryotic organisms, for consistency and simplicity, the phrase genomic target sequence, when used herein generally refers to a eukaryotic organism, such as a defined region of the human genome, for example.

The haploid human genome is constituted by a total number of over 3 billion DNA base pairs and contains an estimate of about 30,000 protein coding sequences. That is, only about 1.5% of the genome encodes for proteins, while the remaining parts contain thousands of RNA genes such as genes encoding for tRNAs, ribosomal RNAs, microRNAs or other noncoding RNAs, regulatory sequences, introns and repetitive sequences. Repetitive sequences of the human genome include, but are not limited to, centromeres, telomers, tandem 10 repeats such as satellite DNA, mini satellite DNA, microsatellite DNA, and interspersed repeats such as SINEs (Short interspersed nuclear elements) and LINEs (Long interspersed nuclear elements). Accordingly, the genomic target sequence of the present disclosure may comprise, but is not limited to, a sequence of a particular gene or a part thereof, and may further include regulatory sequences, non-coding sequences, repetitive or non-repetitive sequences. Further, the genomic target sequence of the presence disclosure refers to a defined gene locus comprising a particular gene.

In general, genes are unevenly distributed across the organism's genome, i.e. across the different chromosomes. That is, the genomic target sequence of the present disclosure may refer to a region of variable length and/or to a region which is spread over different regions of one chromosome, and/or even spread over different chromosomes. For example, a genomic target sequence may refer to one or more individual regions. The genomic target sequence of the present disclosure may also refer to a gene locus (i.e., a specific region on a chromosome where a gene is located) as well. The genomic target sequence of the present disclosure may also comprise regions of varying sizes including, but not limited to, regions with a size of up to 1 MB.

However, it is to be understood that the oligonucleotide probes are directed against (or complementary to) different target sequences, i.e. different portions or subsequences, within the genomic target sequence of the present disclosure. That is, while the set of oligonucleotide probes comprising at least approximately 100 different single oligonucleotide probes is, as a group, directed against a same genomic target sequence (which comprises a particular gene locus, for example) each of the individual oligonucleotide probes is directed against a particular subsequence which lies within this region.

It should also be understood that the set of oligonucleotide probes will in general contain more than one probe directed to the same subsequence. Thus, a number of the probes comprising the total concentration of the probe set, used according to the instant disclosure, will be of the same probe. For example, with reference to FIGS. 1A, 1B, and 1C, the total probe set comprises 1440 probes at a total concentration of 4 µg/ml. It should be understood that in general there will be more than 1 copy of each of the 1440 probes which comprises the total concentration of the probe set.

The term "label" as used herein generally refers to any kind of substance or agent which can be incorporated and/or attached to the oligonucleotide probes of the present disclosure, and which can be used to visualize, detect, analyze and/or quantify the oligonucleotide probe when bound to its target sequence. A label according to the present disclosure may include, but is not limited to, radioisotopes such as, e.g., $^{35}$Sulphur ($^{35}$S), $^{32}$Phosphorus ($^{32}$P), $^{33}$Phosphorus ($^{33}$P), $^{3}$H or $^{14}$C, any fluorescent molecule or fluorophore which can be detected and/or visualized by means of fluorescence analysis such as fluorescein dyes including, but not limited to, carboxyfluorescein (F AM), 6-carboxy-4',5'-dichloro-2 '7'dimethoxyfluorescein (JOE), fluoresceinisothiocyanat (FITC), tetrachlorofluorescein (TET), and hexachlorofluorescein, rhodamine dyes such as, e.g., carboxy-X-rhodamine (ROX), Texas Red and tetramethylrhodamine (T AMRA), cyanine dyes such as pyrylium cyanine dyes, DY548, Quasar 570, or Cy3, Cy5, Alexa 568, and alike. The choice of the fluorescent label is typically determined by its spectral properties and by the availability of equipment for imaging. Fluorescent labels are commercially available from diverse suppliers including, for example, Invitrogen™ (USA). A label of the present disclosure can also be a hapten such as digoxigenin (DIG), biotin, or 2,4-dinitrophenyl (DNP). These labels as well as their detection strategies are well known to the person skilled in the art, and are described in various references such as Jin et al., 2001 (Morphology Methods: Cell and Molecular Biology Techniques, 27-48), Krick, 2002 (Ann. Clin. Biochem. 39: 114-12), or Grzybowski et al., 1993 (Nucleic Acids Research, Vol. 21, No. 8: 1705-1712), which are hereby incorporated by reference in their entirety.

Moreover, the label of the disclosure can either be attached to the oligonucleotide probe by chemical conjugation to a nucleotide or to a non-nucleotide linking reagent (i.e. direct labeling), or by chemical conjugation of the nucleotide or of the non-nucleotide linking reagent to a molecule that can bind a label (i.e. indirect labeling). In indirect labeling, the molecule directly attached to the oligonucleotide probe may be a hapten such as 2,4-dinitrophenyl (DNP), digoxigenin (DIG), or biotin, for example. In direct labeling, the molecule attached to the oligonucleotide probe may be a fluorescent dye, for example. The detection strategies of the different labels according to the present disclosure are further detailed below.

The label of the present disclosure can further be attached to either the 5'-end and/or the 3'end of the oligonucleotide probe, or it can internally be incorporated into the oligonucleotide probe via linkage to one or more modified nucleotide(s) or phosphate(s).

Alternatively, the label of the present disclosure can also be incorporated into the oligonucleotide probe via linkage to one or more non-nucleotide linking reagent(s).

Optionally, the label may be incorporated into the oligonucleotide probe in a 2-step process, for example by introducing reactive groups like amine, azide or alkine groups into the oligonucleotide probes and by coupling the label in a second step via amide bond formation or click chemistry. The term "click chemistry" as used herein generally refers to any bioorthogonal reaction that enables the efficient formation of a specific product within a highly complex chemical environment. For example, it refers to a chemical reaction which allows for the incorporation of one or more reactive tag(s) onto a biomolecular target and the subsequent high selectivity in tag derivatization within a complex biological sample. The principles of click chemistry are generally known in the art and can be found described in Best, M.D. (Biochemistry 2009, 48(28): 6571-6584), which is incorporated by reference in its entirety. Another way of introducing a label of the present disclosure is, for example, to couple the label via the oxidation step during phosphoramidite based oligonucleotide synthesis as described in WO 2007/059816, which is incorporated by reference in its entirety.

As explained above, according to the instant disclosure the set of oligonucleotide probes may be designed as such that each of the individual oligonucleotides is present in one or more copy/copies. The set of oligonucleotide probes may be designed as such that each of the individual oligonucleotide probes is present in equimolar amounts and/or at similar concentrations. Moreover, the set of oligonucleotide probes may be designed such that every copy of each individual oligonucleotide probe having the same identical sequence also contains one or more label(s) at identical positions within the probe. Each of the individual oligonucleotide probes present in either single or multiple copy/copies constitutes one subset of the oligonucleotide probes.

Accordingly, in another embodiment, the set of oligonucleotide probes of the disclosure may comprise one or more subsets of oligonucleotide probes, wherein each subset consists of oligonucleotide probes having identical nucleotide sequences. Further, subsets may also have labels at identical positions.

Additionally, according to the present disclosure, subsets of oligonucleotide probes having identical sequences and labels at identical positions may be advantageous in that the probes biochemical properties may be known such that the most favourable positions for the incorporation of labels may be chosen and, moreover, the unfavourable positions can be prevented.

The oligonucleotide probes of the present disclosure may further be characterized in that the label may be inserted at a defined position during chemical synthesis of the oligonucleotide. That is, a defined number of labels may be incorporated into the molecule by either incorporating modified nucleotides at defined position to which a label is attached, linked, and/or conjugated, or by incorporating non-nucleotide linking reagents which may serve as a platform for label attachment. The insertion of label at defined positions may also include the procedure of incorporating the label during the oxidation step in phosphoramidite based oligonucleotide synthesis. According to some embodiments, the incorporation of label may be such that the labels are evenly distributed across the oligonucleotide probe.

In some embodiments of the present disclosure, the oligonucleotide probes may be designed such that the labels are inserted into the molecule at positions with equal distance to each other, for example at positions with a spacer distance of at least 5, 10, 15, or 20 or more nucleotides to each other. This spacer distance can vary from one subset of oligonucleotide probes to the other, and may also depend on the total length of the individual oligonucleotide probe, i.e. the spacer distance between individual labels may be increased with the total length of the oligonucleotide probe.

Accordingly, in some embodiments, the oligonucleotide probes of the disclosure comprise labels at about equally spaced positions, for example at a spacer distance of at least 5, 10, 15, or 20 nucleotides.

In another embodiment, the oligonucleotide probes may comprise labels at predetermined positions, optionally at positions located at a predetermined distance to each other.

An advantage of positioning labels at particular spaced distances is that negative effects may be avoided which would arise if the labels are positioned too close together (e.g. interference and/or quenching if fluorescent labels are used, for example). Moreover, it may also be possible to avoid having too many labels incorporated or introduced at certain positions which could affect hybridization efficiency.

The term "predetermined" as used herein generally means that the positions at which the label is incorporated, attached, conjugated or linked to can be defined when designing the individual oligonucleotide probes. That is, the term "predetermined" means that the labels are not randomly distributed and/or incorporated as, for example, in the case of enzymatic labeling approaches. One possibility of recognizing and/or determining predetermined label positions is if the distribution of labels within one molecule follows a certain pattern.

In addition, predetermined positions may also be determined when analyzing the distribution of labels within one subset, for example, if each of the oligonucleotide probes of one or more subsets reveals the same pattern of incorporated labels.

As already detailed above, the label can be either directly or indirectly incorporated, attached, conjugated or linked to the individual oligonucleotide probe.

Therefore, in some embodiments, the set of oligonucleotide probes of the disclosure may be characterized in that the label is attached to a base, a sugar, or a phosphate moiety of a nucleotide, either directly or indirectly via a linker.

By attaching the label to a base, a sugar, or a phosphate moiety, potential disruption and/or impairment of complementary base pairing to the target sequence can be reduced to a minimum, and short oligonucleotide probes can be used to achieve efficient binding affinities.

For example, a 2,4-dinitrophenyl (DNP) label may be directly linked to the N4 position of a cytidine. Alternatively, the nucleotide can be modified in order to allow and/or to facilitate linkage of a label. That is, a pyrylium cyanine dye may be covalently linked to a 5-aminoalkyl-modified pyrimidine nucleotide, for example. The direct attachment of a label to the probe may not directly modify a site on the purine or a pyrimidine base that is normally involved in the hydrogen bonding interactions of complementary base pairing.

The term "linker" as referred to herein generally refers to any chemical structure which can serve to couple, conjugate, covalently bind or attach a label to a nucleobase, a sugar or a phosphate moiety of a nucleotide. The linker, according to the present disclosure, may include, but is not limited to, flexible or rigid structures such as, e.g., ethylene glycol linker, hexaethylene glycol linker, propargylamino linker, animo alkyl linker, cyclohexyl linker, aryl linker, ethylene glycol ethynyl and ethyloxyethylamino linker, or alkylamine linker. The label may also be attached via an activated ester to the linker.

In yet another embodiment, the set of oligonucleotide probes of the disclosure is characterized in that the label is attached to a non-nucleotide unit.

An advantage of attaching the label to a non-nucleotide unit is that the design and the synthesis of the individual oligonucleotide probes is sequence independent. That is, the oligonucleotide probes can be designed as such that they contain the label at same positions. Moreover, contrary to the general acceptance in the art, it has surprisingly been found in the context of the present disclosure that the binding efficiencies to the target sequence are still optimal when attaching the labels to non-nucleotide units.

The term "non-nucleotide unit" as used herein generally refers to any reagent or molecule which can conveniently allow single or multiple moieties, such as labels or intercalators, to be linked to a nucleotide probe at any specific pre-selected location(s) therein. A non-nucleotide unit according to the present disclosure may comprise a monomeric unit which can be synthetically coupled with specific nucleotide monomeric units from nucleotide reagents to produce a defined sequence polymer with a backbone comprised of nucleotide and non-nucleotide monomeric units. For example, a non-nucleotide unit of the disclosure can be placed at any desired position within a nucleotide's backbone sequence. A non-nucleotide unit of the disclosure may comprise a ligand which is either a linker-arm moiety which carries a label or which may participate in conjugation reactions once the linker-arm has been deprotected. A non-nucleotide unit of the disclosure may further contain an azide or alkine moiety suitable for click chemistry. Suitable protecting groups which can be used to protect the linker arm functional group during formation of a polymer are known in the art.

A non-nucleotide unit according to the present disclosure may further comprise two coupling groups as to permit its step-wise inclusion into a polymer of nucleotides and non-nucleotide monomeric units, wherein one of this coupling groups is defined as such that it can efficiently couple to the terminus of a growing chain of monomeric units, and the second coupling group is capable of further extending, in a step-wise fashion, the growing chain of mixed nucleotide and non-nucleotide monomers. Non-nucleotide units according to the present disclosure are described in European Patent 0313219, the disclosure of which is hereby incorporated by reference in its entirety.

In a further embodiment, the oligonucleotide probes of the present disclosure comprise a label suitable for detection by means of a chromogenic reaction, by means of a metallographic reaction, or by means of direct or indirect fluorescence analysis.

The term "chromogenic reaction" as used herein includes, but is not limited to, all standard methods known in the art which result in the formation of chromophores at sites of enzymatic activities. That is, in a simple one-step or multi-step chromogenic reaction, a colourless substrate may be enzymatically converted into a coloured product. In the context of the present disclosure, a chromogenic reaction includes any reactions or set of reactions that reveal discrete zones, spots or bands of enzymatic activity which can be investigated, determined and/or analyzed by visual inspection. The detection of biotinylated oligonucleotide probes, for example, commonly employs the colorimetric or chemiluminescent visualization via avidin or streptavidin conjugated to reporter enzymes such as alkaline phosphatase or horse radish peroxidase (HRP). For example, 4-Nitro blue tetrazolium chloride (NBT) and 5-bromo-4-chloro-3-indolyl-phosphate (BCIP) are commonly known in the art to be effective chromogenic substrates for alkaline phosphatase which are converted into a blue coloured product. The detection via chemiluminescent visualization may include any enhanced chemiluminescence (ECL) reaction which involves the emission of light during the horse radish peroxidase (HRP) and hydrogen peroxide-catalyzed oxidation of luminol, for example. The emitted light can be captured on film or by a CCD camera and may serve for qualitative or semi-quantitative analysis. Such detection systems are routinely used in the art and can be purchased from GE Healthcare (USA).

The term "metallographic reaction" as referred to herein generally means any kind of enzymatic or non-enzymatic reaction in which a metal, in the presence of an appropriate metal source and activating agents, is selectively deposited to give a black, highly localized stain. That is, a metallographic reaction refers to an enzyme-catalyzed or metal catalyzed deposition of metal from solution. For example, an enzymatic metallographic reaction according to the present disclosure includes the use of antibody-coupled horse radish peroxidase (HRP) and silver (I) ions in solution. Alternatively, metal particles, e.g. gold particles, can nucleate the highly specific deposition of silver from an appropriate silver salt solution in the presence of a suitable reducing agent. In some embodiments, a non-enzymatic metallographic reaction according to the present disclosure includes the use of oligonucleotide probes labeled directly or indirectly with gold particles and silver (I) ions in solution. Such metallographic reactions have been shown to be highly sensitive both for in situ hybridization (ISH) and immunohistochemistry (IIiC) detection methods, where it readily visualizes endogenous copies of single genes. Because it is used in the conventional brightfield microscope, it does not require fluorescent optics, or dark adaptation on the part of the user. The signal is permanent, and does not have the photobleaching problems associated with fluorescent stains. Such detection systems (e.g. EnzMet™, NanoGold™) may be commercially purchased from diverse suppliers including, e.g., Nanoprobes Inc. (USA)

The term "fluorescence analysis" as used herein generally refers to all sorts of imaging methods known in the art that are suitable to visualize, detect, analyze and/or quantify a fluorescent signal. For example, fluorescence analysis according to the present disclosure includes, but is not limited to, all known methods of deconvolution and confocal fluorescence microscopy including, e.g., multiple-fluorescent-probe microscopy. Oligonucleotide probes can either be directly labeled with fluorescent dyes, and visualized with a fluorescent microscope (direct fluorescent analysis), or oligonucleotide probes can be labeled with a hapten and detected with a fluorescently labeled antibody directed against the hapten and then visualized with a fluorescent microscope (indirect fluorescent analysis). Indirect fluorescence analysis also includes the use of an unconjugated antibody in combination with a fluorescently labeled secondary antibody.

Therefore, in some embodiments, the set of oligonucleotide probes of the present disclosure is characterized in that the label is a fluorescent label or a hapten, in particular a fluorescein dye, a rhodamine dye, or a cyanine dye, or a biotin, digoxigenin or a 2,4-dinitrophenyl moiety, for example.

Dependent on the number of labels present in each of the individual oligonucleotide probes, the set of oligonucleotide probes comprises a varying total number of labels.

As exemplified in Example 3 below, optimal results are obtained for a set of oligonucleotide probes comprising a total number of labels of at least 1000 to 2000, and even a total number of labels of at least 4000 to 8000.

As explained above, in some embodiments, the set of oligonucleotide probes of the disclosure comprises a total number of labels of at least approximately 1000, or at least 2000, or even at least 4000 or at least 8000.

By providing a set of oligonucleotide probes comprising a high number of labels in total, the number of incorporated labels in each of the individual oligonucleotide probes can be reduced with the consequence that each label can be positioned within the molecule in an optimal manner. That is, by incorporating only a limited number of label, undesired quenching effects can, for example, be avoided in case of fluorescent labels, or haptens can 30 be positioned as such that the subsequent detection is optimized due to optimal antibody binding.

The use of oligonucleotide probes for the detection of highly abundant target sequences such as abundantly expressed mRNAs or repetitive genomic sequences including centromeric sequences, is known, but using oligonucleotide probes for the detection of low abundant sequences is known to be difficult, having lower sensistivy and specificity and has been described as disadvantageous.

However, the present disclosure discloses the successful use of oligonucleotide probes for detecting non-repetitive and low abundant genomic sequences. Thus, the present disclosure surprisingly and advantageously provides a system and method for utilizing a set of oligonucleotide probes directed against non-repetitive regions which comprise the genomic target sequence of interest. Accordingly, an embodiment of the present disclosure includes a set of oligonucleotide probes being complementary to non-repetitive regions of the genomic target sequence. Further, it should be understood that the instant disclosure advantageously allows for targeting genomic target sequences that are low abundant genes and being able to visualize and detected these low abundant genes with high sensitivity.

The term "non-repetitive regions" used herein generally refers to any sequence, other than a repetitive DNA element, in a genome of interest. In particular, non-repetitive regions according to the present disclosure mean any region other that the repetitive sequences of the genome (e.g. human genome) including, but are not limited to, centromeres, telomers, tandem repeats (e.g. satellite DNA, minisatellite DNA, and micro satellite DNA), and interspersed repeat elements such as SINEs (short interspersed nuclear elements) and LINEs (long interspersed nuclear elements). Repetitive elements have been found in most eukaryotic genomes analyzed, are mostly present in multiple copies, and do not code for proteins or RNA. Interspersed repeated elements are usually present as single copies and distributed widely throughout the genome.

In a further embodiment, the set of oligonucleotide probes may be complementary to either the sense or the antisense strand of the genomic target sequence.

By using oligonucleotide probes that are either complementary to the sense or the antisense strand of the genomic target sequence, optimal hybridization results by preventing the probes from reannealing.

The term "sense" as used herein means that the sequence of the oligonucleotide probe is the same as the target sequence, e.g. as the coding strand of the genomic sequence. The term "antisense", in contrast, means the sequence of the opposite strand. In the context of the present disclosure, it has been found that oligonucleotide probes that are either complementary to the sense or the antisense strand of the genomic target sequence can be used to detect a genomic target sequence of interest.

The human epidermal growth factor receptor (HER-2) oncogene is a member of the epidermal growth factor receptor or erb gene family and encodes a transmembrane tyrosine kinase receptor that has evolved as a major classifier of invasive breast cancer and as a target for cancer therapy. The HER-2 (C-erbB-2) gene is located on chromosome 17q. HER-2 has been linked to prognosis and response to therapy with the anti-HER-2-humanized monoclonal antibody (trastuzumab) in patients with advanced metastatic breast cancer. The HER-2 status has also been tested for its ability to predict the response of breast cancer to other therapies including hormonal therapies, topoisomerase inhibitors, and anthracyclines. Both morphology-based and molecular-based techniques have been used to measure HER-2 status in breast cancer clinical samples. So far, immunohistochemical (IHC) staining has been the predominant method utilized. Unlike most IHC assays, however, the assessment of HER-2 status is quantitative rather than qualitative, because HER-2 is expressed in all breast epithelial cells. Studies have shown that when a standardized IHC assay is performed on specimens that are carefully fixed, processed, and embedded, there is excellent correlation between gene copy status and protein expression levels.

In the context of the present disclosure, it has surprisingly been found that the set of oligonucleotide probes of the present disclosure is particularly suitable to detect the human epidermal growth factor receptor 2 (human HER-2) gene locus. The human epidermal growth factor receptor 2 (HER2) is highly expressed in approximately 30% of breast cancer patients, and substantial evidence supports the relationship between HER2 overexpression and poor overall survival. Accordingly, there is always a need for an improved method of detecting normal or abnormal human HER-2 gene expression.

Detection of the human epidermal growth factor receptor 2 gene locus according to the present disclosure is, e.g., exemplified in Examples 1 to 3.

It has further been found in the context of the present disclosure that the metallographic detection of a genomic target sequence is favorable when the set of oligonucleotide probes is directed against clustered regions of the target sequence of interest. The term "clustered" as used herein means that the different oligonucleotide probes are directed against individual target sequences which may lie in close proximity to each other. This close proximity may include, but is not limited to, distance of about 50 to 500 nucleotides. Clustering of the oligonucleotide probes further means that these regions are not evenly distributed over the genomic target sequence of interest, but that the oligonucleotide probes may be unevenly distributed, thus covering regions of close proximity within the gene locus (i.e. clusters) as well as regions which are located at more distance. The clustering of oligonucleotide probes according to the present disclosure is exemplified in FIG. 3 (see, pools 2 and 4 for example).

Accordingly, in another embodiment of the present disclosure, the set of oligonucleotide probes is characterized in that the oligonucleotide probes are clustered within the genomic target sequence.

In the context of the present disclosure, it has surprisingly been found that the analysis and/or visualisation of a genomic target sequence is particularly sensitive when using clustered oligonucleotide probes and metallographic detection procedures.

In another embodiment, the set of oligonucleotide probes of the disclosure is characterized in that the oligonucleotide probes are directed against a genomic target sequence, wherein the genomic target sequence comprises the human epidermal growth factor receptor 2 (human HER-2) gene locus.

The term "human epidermal growth factor receptor 2 (human HER-2) gene locus" as referred to herein generally includes all genomic sequences and/or genomic regions which constitute the gene encoding for the human epidermal growth factor receptor 2 (HER2). These sequences may or may not be essential for gene expression. The sequences constituting the human epidermal growth factor receptor 2 (human HER-2) gene locus can be identified by database search including, but not limited to, the NCBI (National Center for Biotechnology Information) GenBank database.

In the context of the present disclosure, it has surprisingly been found that clustering of the oligonucleotide probes is also favourable when applying metallographic detection methods. That is, the clustering of oligonucleotide probes allows for a highly sensitive detection of the gene sequence since it is assumed that the enzyme-mediated deposition of metal is accelerated by the close proximity of labels to each other.

In the context of the present disclosure, it has been demonstrated that a set of oligonucleotide probes comprising at least approximately 100 different oligonucleotide probes can be used to detect a genomic target sequence such as the HER-2 gene locus, for example. Detection of a genomic target sequence, in particular a target sequence comprising the HER-2 gene locus, according to the present disclosure is exemplified in FIGS. 1 to 4.

Accordingly, in another aspect, the present disclosure provides a use of the set of oligonucleotide probes of the present disclosure for detection of a genomic target sequence.

In the context of the present disclosure, the terms "detection" or "detecting" generally mean visualizing, analyzing and/or quantifying the binding of an oligonucleotide probe to its target sequence. Detection, according to the present disclosure, includes, but is not limited to, visual inspection of the probed samples including the use of standard microscopic techniques as well as any kind of fluorescence analysis. The visual inspection of the sample maybe performed after the oligonucleotide probe has been hybridized to its target sequence. In the case of radioactive labels, detection or detecting means the exposure of the probed sample to an X-ray film including the generation of an autoradiogram.

The detection or detecting according to the present disclosure may be carried out by means of chromogenic reactions, metallographic reaction, or by means of direct or indirect fluorescence analysis.

In the context of the present disclosure, it has surprisingly been found that a set of oligonucleotide probes comprising at least approximately 100 different oligonucleotide probes allows for a detection method which provides various advantages over the art. That is, with the set of oligonucleotide probes according to the present disclosure, the genomic target sequence of interest can be detected (i) with a reduced amount of probe, (ii) after a reduced hybridization time, and/or (iii) with reduced background as compared to the methods known and available in the art. Known standard methods for detecting genomic target sequences employ chromogenic in situ hybridization (CISH) and immunohistochemistry (IHC) techniques, such as Ventana Inform™ (from Ventana Medical Systems Inc., USA) and Spot-Light™ (from Zymed Laboratories Inc., CA, USA).

Accordingly in a further aspect, the present disclosure provides a method of detecting a genomic target sequence of interest, said method comprising the steps of
  a) incubating a set of oligonucleotide probes according to the present disclosure with a sample under conditions conducive to the binding of the set of oligonucleotide probes to the genomic target sequence of interest; and
  b) detecting the binding of the oligonucleotide probes to the genomic target sequence.

All aspects and embodiments as defined above also pertain to the method of detecting a genomic target sequence of interest.

The term "under conditions conducive to the binding" generally means conditions under which the labeled oligonucleotide probes of the disclosure can hybridize to its target sequence, i.e. conditions under which the oligonucleotide probes can bind to its target sequence. Particularly, in the context of the present disclosure, conditions conducive to binding means the formation of complementary base pairs between the oligonucleotide probes and the target sequence.

The hybridization between the oligonucleotide probes and the target sequence and thus the formation of complementary base pairs is defined by hydrogen bonding and hydrophobic interactions in equilibrium. That is, annealing and separation of the two complementary strands depend on a variety of factors, including temperature, salt concentrations, pH, the nature of probes and target molecules, and the composition of the hybridization and washing solution. The optimal temperature for hybridization may be in the range of 15-25° C. below the Tm value which defines the melting temperature (Tm) of hybrids, i.e. the temperature at which 50% of the double-stranded nucleic acid chains are separated. Various formulas for calculating Tm values are known to the person in the art. RNA-RNA hybrids are generally 10-15° C. more stable than DNA-DNA or DNA-RNA hybrids and therefore require more stringent conditions for hybridisation and washing. Conditions conducive to the binding according to the present disclosure also include the use of hybridization buffer containing reagents to maximize the formation of duplex and to inhibit non-specific binding of the probe to the tissue or the cells. The concentration of probe must be optimized for each probe and for each tissue. Conditions conducive to the binding also mean incubating the probes with the target sequence for a sufficient period of time as to allow optimal hybridization including the removal of non-bound probes by the application of one or more washing steps.

In the context of the present disclosure, conditions conducive to the binding according to the present disclosure refer to hybridization conditions in which the oligonucleotide probes are incubated with the target sample in solution. That is, conditions conducive to the binding does not mean any conditions in which the oligonucleotide probes are incubated with the target sample while being immobilised, such as in the context of a DNA array. Conditions conducive to the binding according to the present disclosure are described in Example 3.

The analysis of gene expression may be indicative for the presence of diseases, for evaluating different stages of diseases, or for the success or failure of therapeutic treatments. For example, HER-2 gene overexpression has been described to be associated with higher grade and extensive forms of ductal carcinoma, while HER-2 gene amplification has been linked to an adverse outcome in invasive lobular carcinoma.

Moreover, HER-2 gene amplification and protein overexpression have consistently been associated with high tumor grade, DNA aneuploidy, high cell proliferation rate, negative assays for nuclear protein receptors for estrogen and progesterone, p53 mutation, topoisomerase IIa amplification, and alterations in a variety of other molecular biomarkers of breast cancer invasiveness and metastasis. The status of HER-2 gene expression has further been linked to prognosis and response to therapy with the anti-HER-2-humanized monoclonal antibody, trastuzumab (Herceptin®, Genentech, CA, USA).

Accordingly, in some embodiments, the method of detecting a genomic target sequence according to the present disclosure is further characterized in that the detection is for a diagnostic purpose, in particular for a human disease and/or for the effectiveness of a therapeutic treatment in a patient.

The reliability of sensitive detection methods for use in diagnostic purposes and for the evaluation of medical treatments is of particular importance.

In another embodiment, the use of the disclosure or the method of the present disclosure is characterized in that the detection or the detecting is carried out by means of in situ hybridization.

In situ hybridization is a standard method and thus of particular importance.

The term "in situ hybridization" as used in the context of the present disclosure generally refers to any kind of nucleic acid hybridization assay in which a labeled oligonucleotide probe is used to localize a specific DNA or RNA sequence in a portion or section of a tissue (in situ), a cell or, if the tissue is small enough (e.g. plant seeds or *Drosophila* embryos), in the entire organism. Accordingly, in situ hybridization according to the present disclosure means any method of localizing and detecting specific nucleotide sequences in morphologically preserved tissues sections or cell preparations by hybridizing the complementary strand of a nucleotide probe to the sequence of interest.

Three principle types of probes can generally be used for in situ hybridisation, including (i) double-stranded complementary DNA probes, (ii) single-stranded antisense RNA probes, and (iii) synthetic oligonucleotide probes Like other hybridization techniques, probe design, synthesis, and labelling play a key role for successful in situ hybridisation with respect to specificity and sensitivity. There are generally two types of labeled probes that can be used in an in situ hybridization method, namely either directly or indirectly labeled oligonucleotides. Standard labelling procedures generally include the application of enzymatic methods. While double-stranded DNA probes can be labelled by enzymatic nick translation or random primer methods, antisense RNA probes are usually synthesized and labelled by in vitro transcription methods. However, these methods result in the generation of non-defined probe, in which the positions as well as the number of the labels is not defined and not known to the practitioner. Furthermore, enzymatic labelling requires more experimental skills of the person carrying out that labelling as the amount of incorporated label depends from a series of variables including e.g. enzymatic activity and/or amount of label present. Finally, with respect to the exact positions and the amount of incorporated label, each labeling might have a different outcome, since the labelling reaction is the result of a random procedure.

Additionally, oligonucleotide probes used for in situ hybridization are mostly short in length and often less sensitive than longer cDNA or antisense RNA probes. Therefore, so far, oligonucleotide probes have mostly been used for the detection of highly abundant and/or repetitive gene targets, or for mapping the expression of particular gene families in the brain. Gene targets which have been analyzed by in situ hybridization procedures using oligonucleotide probes further include abundant mRNA transcripts such as β-actin, mRNA transcripts of genes which are abundantly expressed in neuroendocrine cells and tumors with secretory granules, and ribosomal rRNA, as well as highly repetitive target sequences such as the centromeric regions of human chromosomes.

However, the use of oligonucleotide probes for the detection and/or the analysis of genes which are present only to a low extend including, e.g., low abundant tumor marker genes, by the routine and high throughput application of hybridization methods would be of particular interest in modem medicine, diagnostics and cancer therapy.

As explained above, labeled oligonucleotide probes for in situ hybridization may either be directly or indirectly labeled. An oligonucleotide may be indirectly labeled by conjugating it to a molecule that can be detected by a secondary molecule or antibody such as, e.g., biotin. Biotin labeled oligonucleotides are frequently used for in situ hybridization techniques and can, e.g., be detected by binding fluorochrome-conjugated avidin to the biotin-labeled and hybridized probe. Another type of indirectly labeled oligonucleotides may include those conjugated to digoxigenin or dinitrophenyl. These labels may, e.g., be detected by fluorochrome-conjugated antidigoxigenin or anti-initrophenyl antibodies. Other oligonucleotides may be directly labeled by covalently attaching fluorochromes to individual nucleotides or non-nucleotide linking reagents at defined position which eliminates the need for secondary detection molecules. The labeling of oligonucleotide probes subsequent to DNA synthesis is often easier than incorporating labeled nucleotides during synthesis. The detection of directly labeled probes, to the contrary, is less time consuming since the use of secondary detection molecules can be omitted. Hence, there are clear advantages and disadvantages to both directly and indirectly labeled probes.

In some embodiments, the oligonucleotide probes of the present disclosure may be labeled with dinitrophenyl and detected by the use of anti-dinitrophenyl antibodies.

The oligonucleotide probe used for in situ hybridisation may be DNA or RNA, or a combination of both, and may or may not be fluorescently labeled. Accordingly, in situ hybridisation of the present disclosure includes both fluorescent in situ hybridization (FISH) as well as all known methods of chromogenic in situ hybridisation (CISH) techniques which can be used in medical diagnostics to assess chromosomal integrity. In situ hybridisation can also be performed by using hapten- or radio-labeled oligonucleotide probes, wherein detection is carried out by the use of fluorophore-labeled antibodies, avidin, or X-ray exposure, for example.

In situ hybridization according to the present disclosure further includes all known procedures of multiplex or multicolor in situ hybridization, i.e. all procedures in which oligonucleotide probes with differently colored fluorescent labels are used, or in which oligonucleotide probes with different haptens and different enzyme/substrate systems are used. These multiple labels can be detected simultaneously or in a series of detection steps. As exemplified in Example 1 of the present disclosure, detection of a genomic target sequence was successfully accomplished in a reduced amount of time (significantly less than 4 hours). Moreover, as compared to methods known in the art (such as the Ventana Inform™ detection method), improved results were obtained even after a hybridization time of 1 hour or 30 minutes. Accordingly, in some embodiments of the method of the present disclosure in that the detecting of step b) is by means of a chromogenic reaction, by means of a metallographic reaction, or by means of direct or indirect fluorescence analysis; and/or the incubating of step a) is completed after at most 4 hours, 3 hours, or 2 hours, or even after at most 1 hour or 30 minutes.

As surprisingly found in the context of the present disclosure, detection of the genomic target sequence could be accomplished in a shorter period of hybridization time as compared to standard detection methods known in the art (see e.g. FIG. 2). Detection of a genomic target sequence by means of indirect fluorescence analysis is exemplified in FIGS. 4A and 4B. The term "completed" as referred to herein is not to be understood as such that the incubating of step a) is essentially finished. It means that an increase in incubation time would not result in a significant improvement or increase of signal. In contrast, the term "completed" rather means the hybridization of the oligonucleotide probes to the target sequence of interest is completed as such that a detectable result can be obtained.

As exemplified in Example 3, it has further been observed in the context of the present disclosure that the choice of different oligonucleotide probe subsets, resulting in diverse oligonucleotide probe "cocktail" compositions, allows for an improved detection as compared to the methods known in the art (e.g. Ventana Inform™).

In a further aspect, the present disclosure provides a method of generating a set of oligonucleotide probes directed against a genomic target sequence of interest, said method comprising the steps of:
  a) designing a set of oligonucleotide probes complementary to at least 100 different regions of a genomic target sequence of interest, in particular wherein the regions comprise non-repetitive sequences; and
  b) synthesizing the set of oligonucleotide probes according to the present disclosure.

All aspects and embodiment as defined above also pertain to the method of generating a set of oligonucleotide probes directed against a genomic target sequence of interest.

An advantage of the present method is that the oligonucleotide probes can be generated in a highly reproducible manner. Moreover, the design of the oligonucleotide probes can be adapted to various different gene sequences.

The term "designing" as used herein generally refers to the identification of different target sequences to which the oligonucleotide probes are complementary. As detailed above, the oligonucleotide probes of the present disclosure may be designed as such that they may be complementary to either the sense or the antisense strand of the target sequence. The oligonucleotide probes may also be designed as such that they are not complementary to any repetitive regions of the human genome. Designing further means that the oligonucleotide probes can form any kind of complementary base pairs with the target sequence of interest including, but not limited to, canonical and non-canonical base pairs and base mismatches. That is, the oligonucleotide probe of the present disclosure may be, but does not necessarily have to be, designed as to reveal a complementarity to the target sequence of 100%. The oligonucleotide probes may also be designed as to reveal less than 100% complementarity to the target sequence, if considered appropriate. The complementarity between the oligonucleotide probe and the target sequence of interest, however, should be sufficient to provide binding to and, consequently, detection of the target sequence of interest. With the increasing numbers of cloned genes, oligonucleotide probes can be designed based on published cDNA sequence and/or gene bank entry. Databases with genomic sequences from diverse organisms include, for example, public databases from the NCBI (National Center of Biological Information, USA).

The term "synthesizing" as used herein refers to the generation of oligonucleotide probes by means of chemical synthesis including, but not limited to, the use of automated DNA and/or RNA synthesizers and phosphoramidite chemistry. Automated DNA or RNA synthesizers are commercially available from diverse suppliers such as, e.g., Applied Biosystems (Darmstadt, Germany), Biolytic (Newark, Calif., USA), or BioAutomation (Plano, Tex., USA). The oligonucleotide probes of the present disclosure may be synthesized in one or more 96-well plates, thus providing for a fast and robust high-throughput synthesis. Chemical synthesis of the oligonucleotide probes in 96-well plate format does not only enable the rapid synthesis of diverse different oligonucleotides, but also the highly efficient and combinatorial selection of different oligonucleotide subsets. As already detailed above, the method of detecting a genomic target sequence of interest according to the present disclosure may further be optimized by the individual and combinatorial choice of at least 100 different oligonucleotide subsets out of a large pool of oligonucleotides generated by multiple 96-cell format synthesis which may then be used to constitute the set of oligonucleotide probes according to the present disclosure. The combinatorial selection of different oligonucleotide probe subsets according to the present disclosure is exemplified in Example 3.

Optionally, the oligonucleotide probes may further be purified by any kind of standard methods applicable and known in the art. Such methods include, but are not limited to, chromatographic methods such as high performance liquid chromatography (HPLC). Optionally, purification of the oligonucleotide probes is carried out via one or more attached protective group(s) such as DMT (dimethoxytrityl), for example. The DMT group may be used for protection of the nucleosides in oligonucleotide synthesis. In principle, each of the oligonucleotide robes may be purified individually and/or separately. The oligonucleotide probes of the disclosure may be purified as a set or as a pool of different subsets. For example, an aliquot of a MWP probe pool consisting of 96 crude oligonucleotides can be purified on a RP 18 HPLC column (Hypersil, 8×240 mm) using a 0.1 M triethylammonium acetate pH 71 acetonitrile gradient. DMT on peak may be collected, desalted via dialysis, evaporated and dissolved in 10 mM Tris pH 8.0. The OD260 nm may be determined by UV measurement.

In another embodiment, the method of the present disclosure is further characterized in that synthesizing of step b) comprises the incorporation of at least one label via a phosphoramidite modified building block, or via the oxidation step during phosphoramidite based oligonucleotide synthesis.

The term "phosphoramidite modified building block" as used herein generally refers to any chemical structure comprising a phosphoramidite or a phosphoramidite derivative which can be used to introduce one or more label(s) into an oligonucleotide molecule. Phosphoramidite modified building blocks can be used to successfully and routinely prepare mono- or polylabelled oligonucleotides directly on an automatic synthesizer by covalently attaching the building block to the growing synthetic oligonucleotide by the same procedure as the classical synthesis. The phosphoramidite modified building block of the present disclosure may refer to a deoxynucleoside phosphoramidite such as N4-aminoalkyl-2'-deoxy-cytidine or C-5 substituted pyrimidine, for example. The deoxynucleoside phosphoramidite may bear a N-protected amino alkyl group at either the C-5 position or the C-4 position of a pyrimidine, the C-8 position of a deoxyadenosine or a deoxyguanosine, or the C-7 position of a 7-deazapurine. Alternatively, the deoxynucleoside phosphoramidite may bear an azide or alkine moiety suitable for click chemistry based incorporation of a label. In particular, the phosphoramidite modified building block of the present disclosure further comprises nonnucleotidic moieties. Optionally, the phosphoramidite modified building block may be labeled before it is incorporated into the oligonucleotide. Labels that may be attached to a phosphoramidite building block of the present disclosure include, but are not limited to, fluorophores, biotin, and 2,4-dinitrophenyl (DNP). Examples of fluorescently labeled phosphoramidite modified building blocks include, but are not limited to, Fluorescein-dT phosphoramidite, cx-FAM phosphoramidite, and Quasar 570-dT phosphoramidite. These compounds can be purchased from diverse suppliers such as, e.g., Invitrogen (Carlsbad, Calif., USA), Biosearch Technologies (Novato, Calif., USA), Biogenex Laboratories (San Ramon, Calif., USA), or Glen Research (Sterling, Calif., USA).

In some embodiments, the phosphoramidite modified building block is a 2,4-dinitrophenyl (DNP)-phosphoramidite.

2,4-dinitrophenyl (DNP)-phosphoramidites are phosphoramidites that are linked to 2,4-dinitrophenyl (DNP). 2,4-dinitrophenyl (DNP) is an inexpensive small label which can be detected immunogenically by the use of monoclonal IgG anti-DNP antibodies. 2,4-dinitrophenyl can be incorporated into oligonucleotides linked to phosphoramidites during solid phase synthesis. Diverse structures of DNP phosphoramidites are described in the art (see e.g. Grzybowski et al., 1993, Nucleic Acid Research, Vol. 21, No. 8: 1705-1712, the disclosure of which is hereby incorporated by reference in its entirety). In order to obtain maximal sensitivity in antibody detection, the DNP moiety may be attached to the phosphoramidite building block via a linker which can be of variable size. The synthesis and the antibody-mediated detection of oligonucleotides containing multiple 2,4-dinitrophenyl reporter groups is also described in the above-incorporated Grzybowski et al.

The label of the disclosure can further be incorporated into the oligonucleotide probe via the oxidation step during phosphoramidite based oligonucleotide synthesis. The process of oxidation during phosphoramidite based oligonucleotide synthesis is described in WO2007/059816, which is incorporated by reference in its entirety.

In yet another aspect, the present disclosure provides a kit comprising a set of oligonucleotide probes according to the present disclosure and, in addition, at least one further component selected from the group consisting of deparaffinization agent, pretreatment agent, washing agent, detection agent and product sheet.

Additionally, a kit, according to the present disclosure, may comprise a variety of standard components such as buffers, antibodies, and/or reagents to stop a particular reaction. The components of the kit may be adjusted to the prevailing intended use, for example, depending on the detection system employed, the cells or tissue or sample examined, the target sequence, the label used, etc. Some of the components are discussed and described below.

The term "deparaffinization agent" as used herein generally refers to any kind of substance which is suitable to remove wax from wax-embedded biological samples. A deparaffinization agent according to the present disclosure may comprise one or more paraffin-solubilizing organic solvent(s), one or more polar organic solvent(s), one or more surfactant(s), and can further optionally comprise water.

The term "pre-treatment agent" as used herein generally refers to any kind of agent or substance which can be used to block unspecific binding sites in solution or which is suitable to improve binding of the oligonucleotide probes to the target sequence when incubated with the sample before addition of the oligonucleotide probe to the hybridization buffer.

The term "washing agent" generally means any kind of liquid composition which can be used to remove unbound oligonucleotide probes after hybridisation. Washing agents of the disclosure may contain mono- or divalent salts such as NaCl, buffer salts such as sodium citrate, and/or formamide at various concentrations. In this respect, higher formamide concentrations and lower NaCl concentrations are usually used for higher stringency. Exemplary washing agents are described in WO 93/06245, which is incorporated by reference in its entirety.

The term "detection agent" as referred to herein generally means any substance or agent which may be relevant for detecting the labelled set of oligonucleotide probes after hybridization to the target sequence. A detection agent of the present disclosure may include, but is not limited to, fluorescently or non-fluorescently labeled antibodies, substrates for enzymatic reaction such as chromogenic substrates for horseradish peroxidase or alkaline phosphatase, or substances such as avidin or streptavidin.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

EXAMPLES

Probe Synthesis

15×96 well-plate DNA probe synthesis of 87mer oligonucleotides labeled with 6 DNP were performed on a Biolytic Dr. Oligo 192 MWP DNA Synthesizer in a 50 nmol scale using standard phosphoramidite chemistry and Biolytic's synthesis cycles. Synthesis was performed in DMT on mode. A 2000 A CPG dT support (Glen Research™, cat. no. 20-2032) was loaded into all wells of the micro well synthesis plate (Orochem™ filter plate 96 well, cat. no. OF 11 00). All other standard reagents needed for phosphoramidite based oligonucleotide synthesis were purchased from Proligo™ or Glen Research™, acetonitrile from Baker™. The quality of oligonucleotide synthesis was regularly checked by color detection of released DMT cation. After the synthesis was completed, oligonucleotides were cleaved and deprotected with ammonia (20 hrs, 40° C.), then evaporated in a speed vac concentrator and resuspended in 600 µl of 10 mM Tris pH 8.0. Thereafter, concentration was determined by OD260nrn measurement. Yield: 7-16 OD260nrn. This crude quality was used to constitute different probe pools.

In Situ Hybridization.

In situ hybridization assay was performed on a Ventana Discovery XT System (Cat. no. 750-701) using Ventana™ reagents for deparaffizpation, pretreatment, washing and stringent washes. Samples were either hybridized with probe compositions according to the present disclosure or with the Ventana INFORM HER2 DNA Probe™ (Ventana, cat. no. 780-4332). Unless otherwise stated, the set of oligonucleotide probes according to the present disclosure consisted of 1440 oligonucleotide probes each comprising 81 nucleotides and carrying 6 non-nucleotidic DNP labels at identical positions with a distance of 16 nucleotides to each other. The total number of labels in this probe was 8640.

Probes were detected either by enzyme metallographic detection, by chromogenic detection, or by indirect fluorescent detection. The probe compositions according to the present disclosure were diluted in hybridization buffer (containing formamide, dextrane sulfate, sodium chloride, sodium citrate in Tris buffer) to a final concentration of 4 µg/ml. The Ventana INFORM HER2 DNA Probe™ (Ventana, cat. no. 780-4332) is provided by the manufacturer as ready-to-use solution in hybridization buffer at a final concentration of 10 µg/ml. Samples were formalin fixed paraffin embedded HER2 3-in-1 Xenograft Control slides (Ventana, cat. no. 783-4332). Each slide carries 3 tissue section of Xenografts derived from Calu3 (high HER2 gene amplification), ZR-75-1 (intermediate HER2 gene amplification) and MCF7 (no HER2 gene amplification) cells, respectively.

Slides were deparaffinized using EZ Prep (Ventana, cat. no. 950-102) for 20 minutes at 65° C. followed by 4×4 minutes at 75° C. Slides were pretreated with reaction buffer (Ventana, cat. no. 950-300) for 3×8 minutes at 90° C. and then digested with Protease 3 (Ventana, cat. no. 760-2020) for 20 minutes at 37° C. The probe was hybridized at 52° C. for 2 hours unless otherwise stated. Stringent washes were performed using SSC (Ventana™, cat. no. 950-110) for 3×8 minutes at 78° C. Slides were then incubated with rabbit anti-DNP antibody (Ventana™, cat. no. 780-4335) for 20 minutes at 37° C. The protocol described above was modified such as that hybridization time was 32 min (FIG. 2A), 1 hour (FIG. 2B) and 2 hours (FIG. 2C), respectively.

Enzyme Metallographic Detection.

The enzyme metallographic detection of the probes was performed using the ultra View SISH Detection Kit (Ventana, cat. no. 780-001), starting with incubation with ultra View SISH-HRP (Ventana ultra View SISH Detection Kit™, cat. no. 780-001) for 16 minutes at 37° C. Slides were then incubated with ultra View SISH Silver Chromogen A, ultra View SISH Silver Chromogen B, and ultra View SISH Silver Chromogen C for 12 minutes at 37° C. (Ventana ultra View SISH Detection Kit™, cat. no. 780-001). Slides were counterstained with Hematoxylin II (Ventana, cat. no. 790-2208) for 4 minutes at 37° C. followed by Bluing Reagent (Ventana, cat. no. 760-2037) for 4 minutes at 37° C. Slides were then washed 2× in mild detergent solution, dehydrated in a series of alcohol dilutions (70%, 96%, 100%) followed by two washes in xylene and then mounted with Permount (Fisher Scientific™, cat. no. SP 15-1 00).

Chromogenic Detection.

Chromogenic detection of the probes was performed using Ventana BlueMap™ reagents (Ventana, cat. no. 760-120). Slides were incubated with alkaline phosphatase conjugated UltraMap anti-rabbit IgG (Ventana cat. no. 760-4314) for 12 min at 37° C., followed by incubation with Activator, BlueMap1 and BlueMap2 (Ventana, cat. no. 760-120) for 20 min at 50° C. Slides were then washed 2× in mild detergent solution, dehydrated in a series of alcohol dilutions (70%, 96%, 100%) followed by two washes in xylene and then mounted with Permount (Fisher Scientific, cat. no. SP15-100).

Fluorescence Analysis.

Indirect fluorescent detection of the probes was performed using DyLight™649 conjugated anti-rabbit IgG for 20 min at 37° C. Slides were counterstained with DAPI (Ventana, cat. no. 760-4196) for 8 min at room temperature. Slides were then washed 2× in mild detergent solution, dehydrated in a series of alcohol dilutions (70%, 96%, 100%) followed by two washes in xylene and then mounted with Permount (Fisher Scientific, cat. no. SP 15-1 00). Fluorescent microscopy was performed with a fluorescence microscope (Leica DM5500) using a halogen fluorescence lamp (Leica EL6000) and a Cy5 fluorescence filter cube (excitation 620 nm, dichromatic mirror 660 nm, suppression 700 nm) for visualization of HER2 gene sequence signals and a DAPI fluorescence filter cube (excitation 360 nm, dichromatic mirror 400 nm, suppression 470 nm) for visualization of the counterstain. Images were taken with a CCD camera (Leica DFC 350FX) using a 60× objective.

Example 1

Figure 1B:
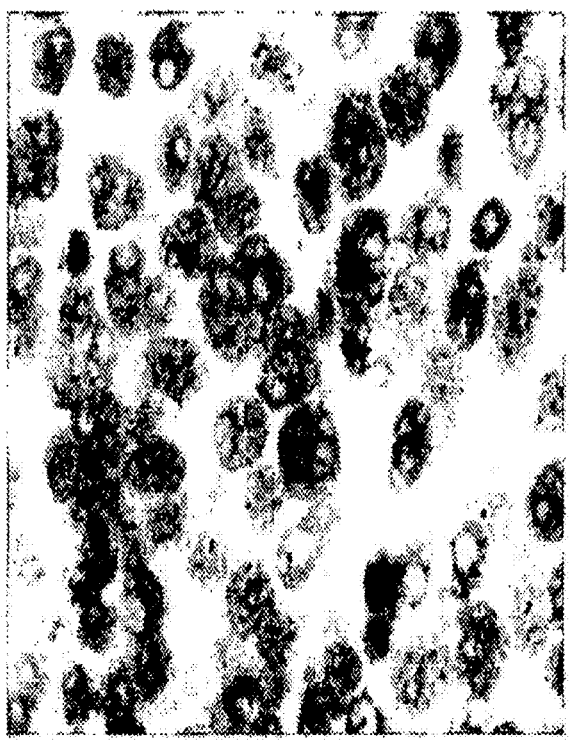
FIG. 1B presents in situ hybridization results, using DNP-labeled oligonucleotide probes at various concentrations, for HER-2 genomic gene sequences in Xenografts derived from ZR-75-1 cells. The left panel presents results obtained utilizing the HER-2/neu probe at a concentration of 10 µg/ml from the Ventana Inform™ detection system (from Ventana Medical Systems, Inc., U.S.A., Cat. No. 780-001). The right panel presents results obtained utilizing a set of 1440 different DNP-labeled oligonucleotide probes at a concentration of 4 µg/ml (each oligonucleotide probe comprised 81 nucleotides and 6 labels).
Figure 1B:
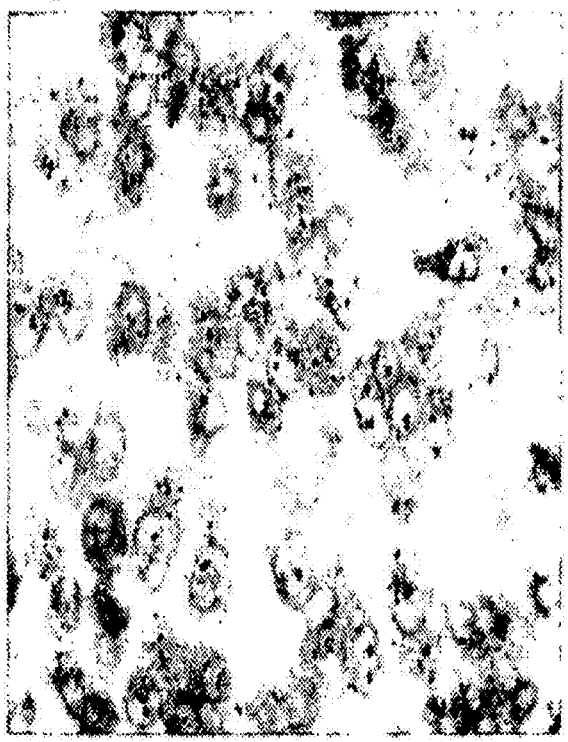
Figure 1C:
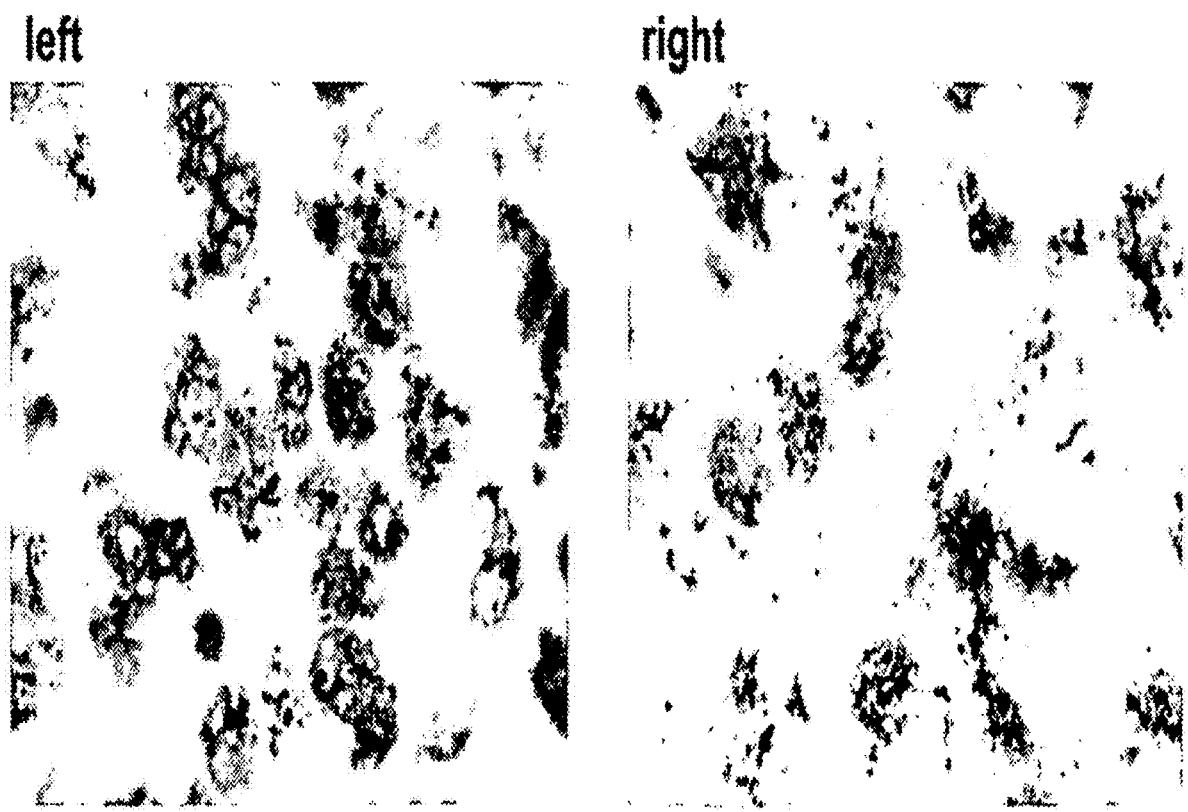
FIG. 1C presents in situ hybridization results, using DNP-labeled oligonucleotide probes at various concentrations, for HER-2 genomic gene sequences in Xenografts derived from MCF7 cells. The left panel presents results obtained utilizing the HER-2/neu probe at a concentration of 10 µg/ml from the Ventana Inform™ detection system (from Ventana Medical Systems, Inc., U.S.A., Cat. No. 780-001). The right panel presents results obtained utilizing a set of 1440 different DNP-labeled oligonucleotide probes at a concentration of 4 µg/ml (each oligonucleotide probe comprised 81 nucleotides and 6 labels).

With reference to FIGS. 1A, 1B, and 1C, in situ hybridization results, using DNP-labeled oligonucleotide probes at various concentrations, for HER-2 genomic gene sequences in Xenografts derived from Calu3 cells (FIG. 1A), ZR-75-1 cells (FIG. 1B), and MCF7 cells (FIG. 1C) are presented. The various cell lines show differing gene amplification (Calu3—no gene amplification; ZR-75-1 cells—low gene amplification; MCF7 cells—high gene amplification). As demonstrated, at a hybridization time of 2 hours, the set of oligonucleotide probes according to the present disclosure resulted in similar signal intensity for all cell lines, even at the lower probe concentration (4 µg/ml vs. 10 µg/ml) when compared to the Ventana INFORM HER2 DNA Probe™ (Ventana Medical Systems Inc., USA).

Example 2

Figure 2A:
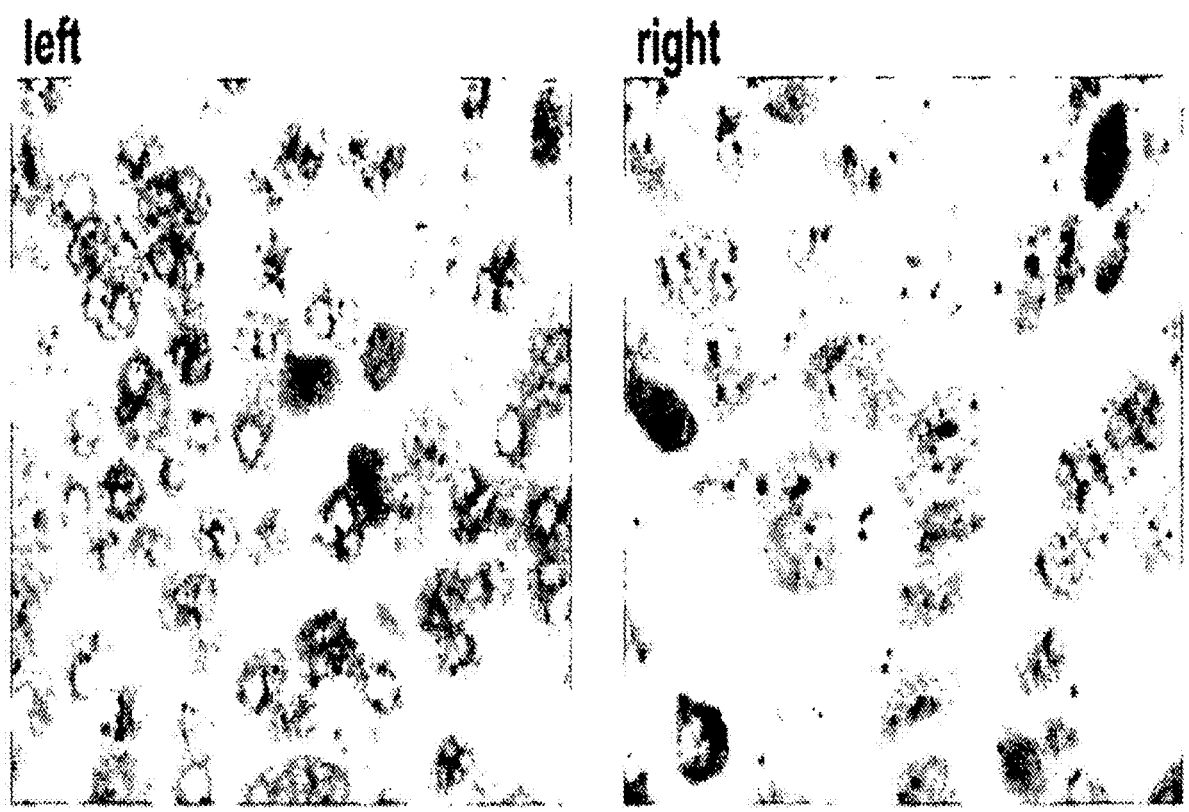
FIG. 2A presents in situ hybridization results, using DNP-labeled oligonucleotide probes, for HER-2 genomic gene sequences in Xenografts derived from ZR-75-1 cells. These results were obtained following a 32 minute hybridization period with the oligonucleotide probes using enzyme metallographic detection. The left panel presents results obtained utilizing the HER-2/neu probe from the Ventana Inform™ detection system (from Ventana Medical Systems, Inc., U.S.A., Cat. No. 780-001). The right panel presents results obtained utilizing a set of 1440 different DNP-labeled oligonucleotide probes (each oligonucleotide probe comprised 81 nucleotides and 6 labels).
Figure 2B:
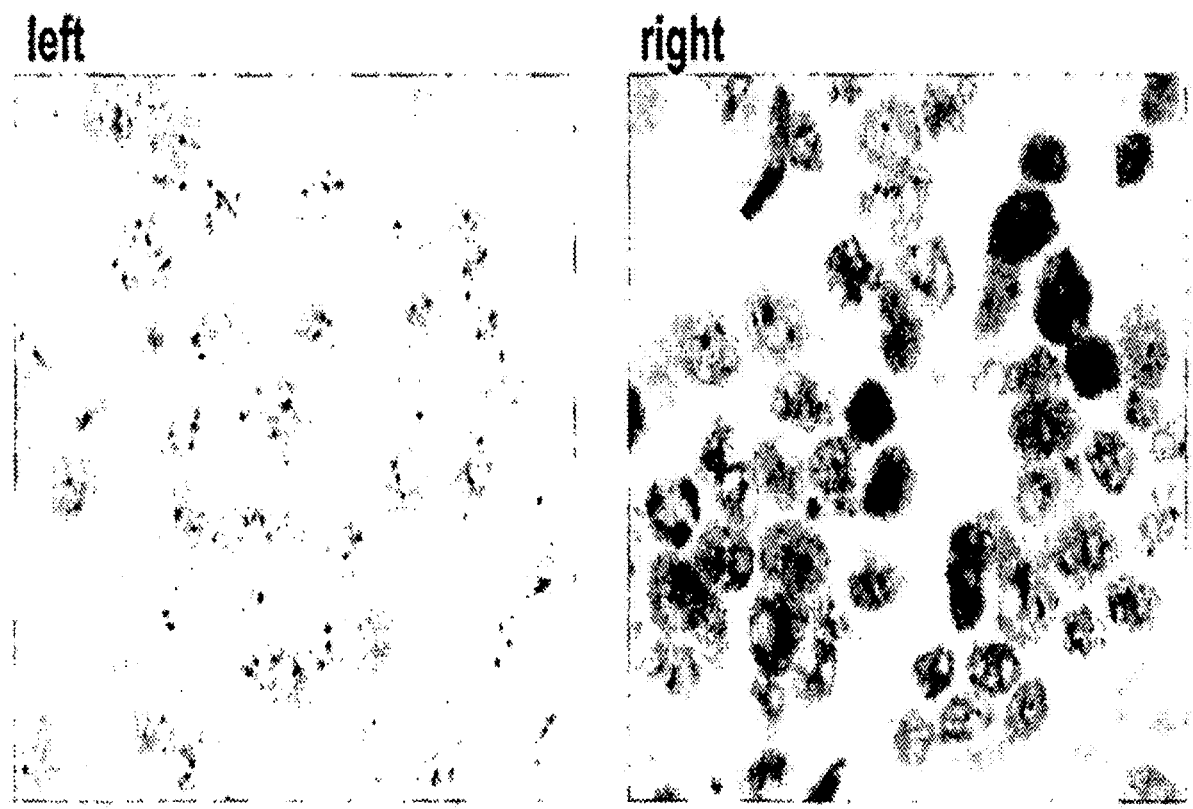
FIG. 2B presents in situ hybridization results, using DNP-labeled oligonucleotide probes, for HER-2 genomic gene sequences in Xenografts derived from ZR-75-1 cells. These results were obtained following a 1 hour hybridization period with the oligonucleotide probes using enzyme metallographic detection. The left panel presents results obtained utilizing the HER-2/neu probe from the Ventana Inform™ detection system (from Ventana Medical Systems, Inc., U.S.A., Cat. No. 780-001). The right panel presents results obtained utilizing a set of 1440 different DNP-labeled oligonucleotide probes (each oligonucleotide probe comprised 81 nucleotides and 6 labels).
Figure 2C:
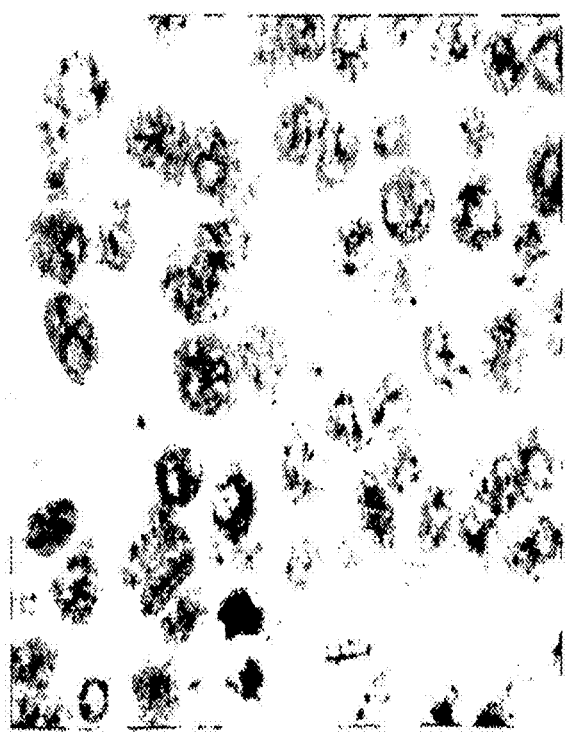
FIG. 2C presents in situ hybridization results, using DNP-labeled oligonucleotide probes, for HER-2 genomic gene sequences in Xenografts derived from ZR-75-1 cells. These results were obtained following a 2 hour hybridization period with the oligonucleotide probes using enzyme metallographic detection. The left panel presents results obtained utilizing the HER-2/neu probe from the Ventana Inform™ detection system (from Ventana Medical Systems, Inc., U.S.A., Cat. No. 780-001). The right panel presents results obtained utilizing a set of 1440 different DNP-labeled oligonucleotide probes (each oligonucleotide probe comprised 81 nucleotides and 6 labels).
Figure 2C:
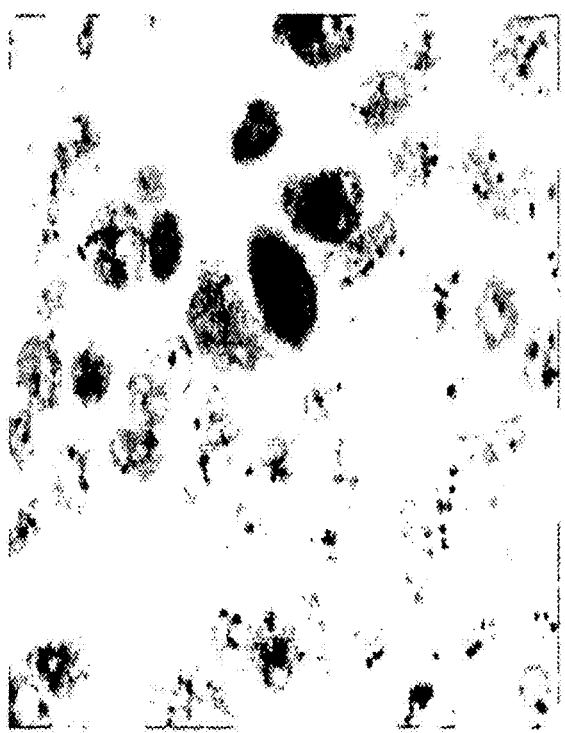

With reference to FIGS. 2A, 2B, and 2C, in situ hybridization results, using DNP-labeled oligonucleotide probes, for HER-2 genomic gene sequences in Xenografts derived from ZR-75-1 cells are presented. These results were obtained following differing lengths of hybridization with the oligonucleotide probes and using enzyme metallographic detection. As demonstrated in these Figures, using the set of oligonucleotide probes according to the present disclosure, a more intense staining signal was observed after 32 minutes or after 1 hour of hybridization, as compared to the Ventana INFORM HER2 DNA Probe™, at a lower concentration (4 µg/ml vs. 10 µg/ml). While the set of oligonucleotide probes according to the present disclosure resulted in optimal staining after a hybridization time of only 32 minutes, optimal staining using the INFORM™ HER2 DNA Probe was achieved only after 2 hours, and suboptimal staining was achieved after 1 hour (see FIG. 2B).

Example 3

Figure 3A:
FIG. 3A is a schematic representation of the various oligonucleotide probe sets used in the in situ hybridization assays for HER-2 genomic gene sequences in Xenografts derived from ZR-75-1 cells. Each box represents a 96-well plate comprising 96 different oligonucleotide probes.
Figure 3A:
Figure 3A:
Figure 3A:
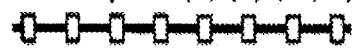
Figure 3A:
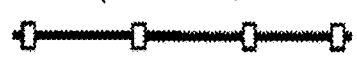
Figure 3A:
Figure 3A:
Figure 3A:
Figure 3A:
Figure 3A:
Figure 3B:
FIG. 3B presents in situ hybridization results, using various sets of DNP-labeled oligonucleotide probes, for HER-2 genomic gene sequences in Xenografts derived from ZR-75-1 cells. The upper left panel presents results obtained utilizing the HER-2/neu probe from the Ventana Inform™ detection system (from Ventana Medical Systems, Inc., U.S.A., Cat. No. 780-001). The lower left panel presents results obtained utilizing the DNP-labeled oligonucleotide probes of Pool 2 (having 4608 labels), as shown in FIG. 3A. The upper right panel presents results obtained utilizing the DNP-labeled oligonucleotide probes of Pool 1 (having 8640 labels), as shown in FIG. 3A. The lower left panel present results obtained utilizing the DNP-labeled oligonucleotide probes of Pool 4 (having 4608 labels), as shown in FIG. 3A.
Figure 3B:
Figure 3B:
Figure 3B:
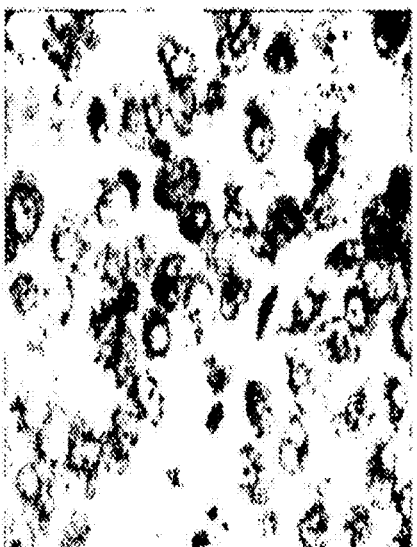

With reference to FIGS. 3A and 3B, when using metallographic detection, the clustering of oligonucleotide probe subsets at both ends of the target locus (leaving the middle part of the target locus unlabeled) gives a more intense staining than an even distribution of oligonucleotide probe subsets over the entire target locus (see FIGS. 3A and 3B, Pool 2 vs. Pool 4). It is noted that the total number of labels, however, is equal in both pools. This illustrates an advantage of the set of oligonucleotide probes of the present disclosure in that it provides the possibility to design optimal compositions of oligonucleotide sets (or subsets) in order to obtain optimal signal intensity while minimizing the number of necessary oligonucleotide probe sets (or subsets).

Example 4

Figure 4A:
FIG. 4A presents in situ hybridization results, using DNP-labeled oligonucleotide probes, for HER-2 genomic gene sequences in Xenografts derived from MCF7 cells. These results were obtained with using indirect fluorescent detection and DyLight™649 conjugated anti-rabbit IgG in Xenografts derived from MCF7 cells. The hybridization of the probe to the HER-2 gene locus was visualized with a Cy5 filter; the counterstain was visualized through a DAPI filter, and the overlay was Cy5 and DAPI filter.
Figure 4A:
Figure 4A:
Figure 4B:
FIG. 4B presents in situ hybridization results, using DNP-labeled oligonucleotide probes, for HER-2 genomic gene sequences in Xenografts derived from Calu cells. These results were obtained with using indirect fluorescent detection and DyLight™649 conjugated anti-rabbit IgG in Xenografts derived from Calu cells. The hybridization of the probe to the HER-2 gene locus was visualized with a Cy5 filter; the counterstain was visualized through a DAPI filter, and the overlay was Cy5 and DAPI filter.
Figure 4B:
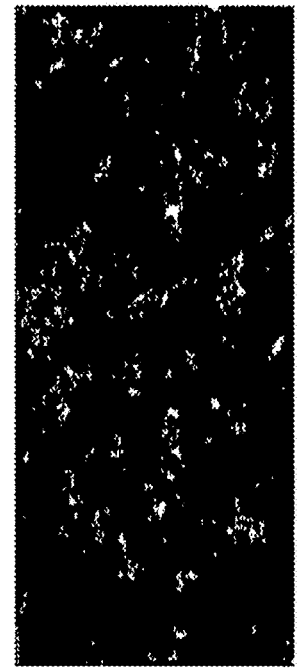
Figure 4B:

With reference to FIGS. 4A and 4B, the set of oligonucleotide probes according to the present disclosure can be visualized using indirect fluorescent detection. FIGS. 4A and 4B demonstrate HER2 gene amplification in Xenografts dervived from MCF7 (FIG. 4A) and Calu (FIG. 4B) cells by in situ hybridization with DNP-labeled oligonucleotide probes. FIG. 4A shows no (or very low) gene amplification of HER2 genomic genomic sequence using DyLight™649 conjugated anti-rabbit IgG in Xenografts derived from MCF7 cells. FIG. 4B shows high gene amplification of HER2 genomic genomic sequence using DyLight™649 conjugated anti-rabbit IgG in Xenografts derived from Calu cells.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

The invention claimed is:

1. A kit for the detection of a genomic target sequence of interest, wherein the genomic target sequence of interest is a region which is spread over different regions of one chromosome or spread over different chromosomes, the kit comprising: a first probe set comprising at least 100 different first oligonucleotide probes, wherein each of the first oligonucleotide probes of the first probe set comprises a different nucleotide sequence complementary to a different subsequence of the genomic target sequence of interest; wherein each of the first oligonucleotide probes of the first probe set comprises at least three first labels; and wherein the at least three first labels in each of the first oligonucleotide probes of the first probe set are the same, and wherein each of the at least three first labels are attached to one of a base, a sugar, and a phosphate moiety of a nucleotide in each of the first oligonucleotide probes at about equally spaced positions.

2. The kit of claim 1, further comprising a first detection agent.

3. The kit of claim 2, wherein the first detection agent is used for specifically detecting hybridization of at least one of the first oligonucleotide probes to at least one of the subsequences of the genomic target of interest in a chromogenic reaction or a metallographic reaction.

4. The kit of claim 1, wherein the at least three first labels are selected from the group consisting of a hapten, a radioisotope, biotin, digoxigenin, and a 2,4-dinitrophenyl moiety.

5. The kit of claim 1, wherein the first probe set comprises at least 200 different oligonucleotide probes.

6. The kit of claim 1, wherein the first probe set comprises at least 500 different oligonucleotide probes.

7. The kit of claim 1, wherein the at least three first labels are attached indirectly to the base, the sugar, or the phosphate moiety of the nucleotide in each of the first oligonucleotide probes via a linker.

8. The kit of claim 1, wherein each of the first oligonucleotide probes has a substantially similar length.

9. The kit of claim 1, wherein each of the first oligonucleotide probes has an identical length.

10. The kit of claim 1, wherein the at least three first labels are positioned at identical positions in each of the first oligonucleotide probes.

11. The kit of claim 1, wherein the distance between the one first label of the at least three first labels and the its adjacent first label of the at least three first labels is about 10 nucleotides to about 20 nucleotides.

12. The kit of claim 1, wherein each of the first oligonucleotide probes has a length ranging from about 20 nucleotides to about 200 nucleotides.

13. The kit of claim 1, wherein each of the first oligonucleotide probes further comprises a non-nucleotide unit.

14. The kit of claim 1, wherein the genomic target sequence of interest comprises a HER2 gene locus.

15. The kit of claim 1, further comprising a second probe set comprising at least 100 different second oligonucleotide probes, wherein each of the second oligonucleotide probes of the second probe set comprises a different nucleotide sequence complementary to a different subsequence of the genomic target sequence of interest; wherein each of the second oligonucleotide probes of the second probe set comprise at least three second labels; and wherein the at least three second labels in each of the second oligonucleotide probes of the second probe set are the same, and wherein the at least three second labels are different from the at least three first labels.

16. The kit of claim 15, further comprising a second detection agent.

17. A kit for the detection of a genomic target sequence of interest, wherein the genomic target sequence of interest is a region which is spread over different regions of one chromosome or spread over different chromosomes, the kit comprising: a first probe set comprising at least 100 different first oligonucleotide probes, wherein each of the first oligonucleotide probes of the first probe set comprises a different nucleotide sequence complementary to a different subsequence of the genomic target sequence of interest; wherein each of the first oligonucleotide probes of the first probe set comprises at least three first labels; wherein the at least three first labels in each of the first oligonucleotide probes of the first probe set are the same, and wherein the genomic target sequence of interest comprises a HER2 gene locus.

18. The kit of claim 17, further comprising a first detection agent, wherein the first detection agent is used for specifically detecting hybridization of at least one of the first oligonucleotide probes to at least one of the subsequences of the genomic target of interest in a chromogenic reaction or a metallographic reaction.

19. The kit of claim 17, wherein the at least three first labels are selected from the group consisting of a hapten, a radioisotope, biotin, digoxigenin, and a 2,4-dinitrophenyl moiety.

* * * * *

SEQUENCE LISTING

```
<160> NUMBER OF SEQ ID NOS: 5

<210> SEQ ID NO 1
<211> LENGTH: 81
<212> TYPE: DNA
<213> ORGANISM: Artificial Sequence
<220> FEATURE:
<223> OTHER INFORMATION: Her2 Probe 0001

<400> SEQUENCE: 1
tcacctttcg acctctgctc caaaacacac tctttgtttt tcttgagaaa cctgctgata      60
aatatctgta cttcgatgct t                                               81

<210> SEQ ID NO 2
<211> LENGTH: 81
<212> TYPE: DNA
<213> ORGANISM: Artificial Sequence
<220> FEATURE:
<223> OTHER INFORMATION: Her2 Probe 0002

<400> SEQUENCE: 2
tacgtttaca cacagcccta aatttattca ggcgtctctt ctggaacgag atgtaagctg      60
attttgtatt catttgcccc t                                               81

<210> SEQ ID NO 3
<211> LENGTH: 81
```

```
<212> TYPE: DNA
<213> ORGANISM: Artificial Sequence
<220> FEATURE:
<223> OTHER INFORMATION: Her2 Probe 0003

<400> SEQUENCE: 3
cctgagcttt catcctgaag gcgaggagaa gctagatccg ccacaaaagg ataagccctt    60
ccccaccact aacggaggaa t                                              81

<210> SEQ ID NO 4
<211> LENGTH: 81
<212> TYPE: DNA
<213> ORGANISM: Artificial Sequence
<220> FEATURE:
<223> OTHER INFORMATION: Her2 Probe 0004

<400> SEQUENCE: 4
caggcctcgc gccgctggat attaaacctg ccggccggta gctttcggct ccctgcgga     60 aaccgccatt ttttttttat t                                              81

<210> SEQ ID NO 5
<211> LENGTH: 81
<212> TYPE: DNA
<213> ORGANISM: Artificial Sequence
<220> FEATURE:
<223> OTHER INFORMATION: Her2 Probe 0005

<400> SEQUENCE: 5
atgactagat tttcaaaggc tattggtatc aggagtgtct tatgaaagat aagtttaacc    60
tgagatacta gatgcaataa t                                              81
```